United States Patent [19]
Balko

[11] 4,289,778
[45] Sep. 15, 1981

[54] 2-(SUBSTITUTED IMINO)-N-(3-SUBSTITUTED PHENYL)-3-THIAZOLIDINECARBOTHIOAMIDES

[75] Inventor: Terry W. Balko, Waldron, Ind.

[73] Assignee: Eli Lilly and Company, Indianapolis, Ind.

[21] Appl. No.: 864,998

[22] Filed: Dec. 27, 1977

[51] Int. Cl.³ .......................................... C07D 277/04
[52] U.S. Cl. ................... 424/263; 424/267; 424/270; 424/248.5; 424/248.51; 548/190; 548/193; 546/280; 546/336; 544/58.5; 544/82; 546/209
[58] Field of Search ................ 260/306.7 T; 424/263, 424/267, 270, 248.5, 248.51; 548/193, 194, 190; 546/280, 209, 336; 544/58.5, 82

[56] References Cited

FOREIGN PATENT DOCUMENTS 7417059 7/1975 Netherlands .

OTHER PUBLICATIONS

Stacy et al., J. Org. Chem., 23, 1760 (1958).
Yamamutu et al., C. Abstracts, 1360 39Z (1974).
Klayman et al., J. Het. Chem. 5 517 (1968).
Cherbuliez et al., Helv. Chim. Acta., 49, 807 (1966).
Yamamoto et al., Chem. Pharm. Bull. 23, 2134 (1975).
Rabinowitz et al., J. Org. Chem., 34, 372 (1969).

Primary Examiner—Nicholas S. Rizzo
Attorney, Agent, or Firm—Karen B. O'Connor; Arthur R. Whale

[57] ABSTRACT 2-(Substituted imino)-N-(3-substituted phenyl)-3-thiazolidinecarbothioamides, useful as insecticides.

97 Claims, No Drawings

2-(SUBSTITUTED IMINO)-N-(3-SUBSTITUTED PHENYL)-3-THIAZOLIDINECARBOTHIOAMIDES

BACKGROUND OF THE INVENTION

This invention relates to thiazolidines. More particularly, this invention relates to 2-(substituted imino)-N-(3-substituted phenyl)-3-thiazolidinecarbothioamides which are useful as insecticides.

Compounds containing the thiazolidine nucleus are not new; see, e.g., G. W. Stacy et al., *J. Org. Chem.*, 23, 1760 (1958). 2-Iminothiazolidines also are known, most often in conjunction with an N-substituted thiocarbamoyl group; see, e.g., D. L. Klayman et al., *Tetrahedron Lett.*, 1967, 281; D. L. Klayman et al., *J. Heterocycl. Chem.*, 5, 517 (1968); Y. Yamamoto et al., *Kyoritsu Yakka Daigaku Kenkyu Nempo*, 1973, 46 and 53 [*Chem. Abstr.*, 81, 136039z (1974)]; and D. L. Klayman et al., *J. Org. Chem.*, 40, 2000 (1975).

It should be noted that in the preparation of 2-iminothiazolidines having a thiocarbamoyl substituent, the reaction usually employed can give either of two products, a 2-imino-3-thiocarbamoylthiazolidine or an N-(2-thiazolin-2-yl)thiourea, and the identity of the product has been in dispute. Thus, E. Cherbuliez et al., *Helv. Chim. Acta*, 49, 807 (1966), reported that the reaction of an aminoalkyl sulfuric monoester with an excess (or two equivalents) of an isothiocyanate in the presence of two equivalents of base usually gives a thiazoline, although N-methylcolamine sulfuric monoester reacts with one equivalent of phenyl isothiocyanate and two equivalents of base to give 2-phenylimino-3-methylthiazolidine. According to J. Rabinowitz, *Helv. Chim. Acta*, 52, 255 (1969), in those cases where the cyclization of β-(N-thiocarbamoylamino)ethyl(or propyl) alcohols (or their orthophosphoric or sulfuric monoesters) gives 5-membered rings, the C=N double bond is always endocyclic.

On the other hand, Y. Yamamoto et al., *Chem. Pharm. Bull.* (Tokyo), 23, 2134 (1975), reported that the reaction of 2-alkylamino-2-thiazolines with an isothiocyanate gave the 3-N-alkylthiocarbamoyl-2-alkylimino-thiazolidines, and not the 2-thiazolin-2-ylthioureas reported by Cherbuliez et al., supra.

3-N-Alkylthiocarbamoyl-2-iminothiazolidines are reported to possess anti-inflammatory activity. According to Netherlands Patent Specification No. 7417059, 3-alkyl-2-thiocarbamoylimino-3-thiazolines are active as insecticides, acaricides, and ovicides.

SUMMARY OF THE INVENTION

In accordance with the present invention, 2-(substituted imino)-N-(3-substituted phenyl)-3-thiazolidinecarbothioamides are provided having the formula,

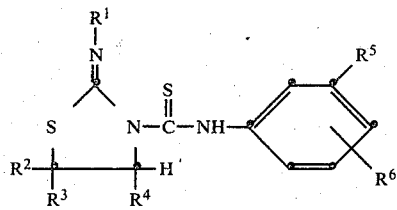

wherein $R^1$ represents (A) $C_1$–$C_{18}$ alkyl;
(B) $C_2$–$C_{18}$ alkenyl;
(C) $C_4$–$C_{18}$ alkadienyl;
(D) $C_3$–$C_{12}$ cycloalkyl, optionally substituted with either one or two $C_1$–$C_3$ alkyl groups;
(E) $C_5$–$C_{12}$ cycloalkenyl, optionally substituted with either one or two $C_1$–$C_3$ alkyl groups;
(F) $C_6$–$C_{12}$ cycloalkadienyl, optionally substituted with either one or two $C_1$–$C_3$ alkyl groups;
(G) phenyl, optionally substituted with from one to three groups selected from the group consisting of
  (1) $C_1$–$C_6$ alkyl,
  (2) $C_1$–$C_6$ alkoxy,
  (3) $C_1$–$C_6$ alkylthio,
  (4) trifluoromethyl,
  (5) halo, and
  (6) cyano;
(H) (cycloalkyl)alkyl, containing no more than about 18 carbon atoms, in which the cycloalkyl moiety is as defined hereinabove;
(I) phenylalkyl, containing no more than about 18 carbon atoms, in which the phenyl moiety is as defined hereinabove;
(J) diphenylalkyl, containing no more than about 18 carbon atoms, in which each phenyl moiety is as defined hereinabove;
(K) pyridyl, optionally substituted with either one or two groups selected from the group consisting of
  (1) $C_1$–$C_3$ alkyl,
  (2) $C_1$–$C_3$ alkoxy, or
  (3) halo;
(L) piperidino, optionally substituted with either one or two $C_1$–$C_3$ alkyl groups;
(M) morpholino;
(N) pyrazinyl, optionally substituted with either one or two $C_1$–$C_3$ alkyl groups;
(O) pyridylalkyl, containing no more than about 17 carbon atoms, in which the pyridyl moiety is as defined hereinabove;
(P) piperidinoalkyl, containing no more than about 17 carbon atoms, in which the piperidino moiety is as defined hereinabove;
(Q) morpholinoalkyl, containing no more than about 16 carbon atoms;
(R) pyrazinylalkyl, containing no more than about 16 carbon atoms, in which the pyrazinyl moiety is as defined hereinabove;
(S) tetrahydrofurylalkyl, containing no more than about 17 carbon atoms; and
(T) substituted amino, having the formula

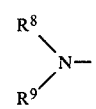

in which $R^8$ and $R^9$ independently are selected from the group consisting of hydrogen, $C_1$–$C_{18}$ alkyl, phenyl, and phenylalkyl, wherein the phenyl and phenylalkyl moieties are as defined hereinabove, provided that at least one of $R^8$ and $R^9$ is other than hydrogen;

$R^2$ and $R^3$ independently are selected from the group consisting of (A) hydrogen,
(B) $C_1$–$C_3$ alkyl, and
(C) phenyl, with the proviso that when one of $R^2$ and $R^3$ is phenyl, the other of $R^2$ and $R^3$ is hydrogen;

$R^4$ represents
(A) hydrogen or
(B) $C_1$–$C_3$ alkyl;

$R^5$ represents
(A) halo,
(B) trifluoromethyl,
(C) cyano, or
(D) 1,1,2,2-tetrafluoroethoxy; and $R^6$ represents
(A) hydrogen,
(B) halo, or
(C) $C_1$–$C_3$ alkyl; with the provisos that when $R^5$ is bromo, $R^1$ can not be 3-bromophenyl; when $R^5$ is cyano, $R^1$ can not be 3-cyanophenyl; when $R^5$ is halo and $R^6$ is halo, $R^6$ can not be in the 2-position; and when $R^5$ is halo and $R^6$ is $C_1$–$C_3$ alkyl, $R^6$ can not be in the 4-position.

A preferred group of compounds comprises the compounds of the above formula wherein $R^1$ represents
(1) phenyl, optionally monosubstituted with $C_1$–$C_3$ alkyl, $C_1$–$C_4$ alkoxy, chloro, or trifluoromethyl,
(2) cycloalkyl,
(3) diphenylalkyl,
(4) phenylamino, or
(5) 3-pyridyl;

$R^2$ and $R^3$ independently are either hydrogen or methyl;
$R^4$ is hydrogen, methyl, or ethyl;
$R^5$ is chloro, bromo, or trifluoromethyl; and
$R^6$ is hydrogen.

A most preferred group of compounds comprises the compounds of the above formula wherein $R^1$ represents
(1) phenyl, optionally monosubstituted with $C_1$–$C_3$ alkyl or $C_1$–$C_4$ alkoxy in the 2- or 4-position, or trifluoromethyl in the 3- or 4-position, or
(2) $C_6$–$C_8$ cycloalkyl; one of $R^2$ and $R^3$ is hydrogen or methyl and the other of $R^2$ and $R^3$ is hydrogen;
$R^4$ is hydrogen or methyl;
$R^5$ is chloro; and
$R^6$ is hydrogen;
with the proviso that at least two of $R^2$, $R^3$, and $R^4$ are hydrogen.

The present invention also provides a method for reducing or eradicating a population of an insect species which comprises administering to the insect by ingestion an insecticidally-effective amount of a compound of the above formula. The compounds of the present invention are especially effective against the insect species *Epilachna varivestis*.

Additionally, the present invention provides an insecticidal composition which comprises an insecticidally-effective amount of a compound of the above formula and an agriculturally-acceptable carrier.

DETAILED DESCRIPTION OF THE INVENTION

In the above formula, the various chemical groups have their usual meanings. For the sake of clarity, however, examples of the various generally-named groups will be given.

The term "$C_1$–$C_{18}$ alkyl" includes, among others, methyl, ethyl, propyl, isopropyl, butyl, isobutyl, pentyl, neopentyl, 1-methylbutyl, hexyl, isohexyl, 2,3-dimethylbutyl, 1-ethylpentyl, 2-ethyl-3-methylbutyl, 2-ethylhexyl, 6-methylheptyl, nonyl, 2,4,4-trimethylhexyl, decyl, 7,7-dimethyloctyl, 1-propylheptyl, 1,1-dimethyloctyl, undecyl, 3-ethyl-2,6-dimethylheptyl, 10-methylundecyl, 5-ethyl-2,6-dimethyloctyl, tridecyl, 2,2,6,6,7-pentamethyloctyl, 9-ethyldodecyl, pentadecyl, 5-sec-butyl-2,7-dimethylnonyl, 14-methylpentadecyl, 3-propyl-8-ethyldodecyl, octadecyl, 1-methylheptadecyl, and the like.

The terms "$C_2$–$C_{18}$ alkenyl" and "$C_4$–$C_{18}$ alkadienyl" include, among others, vinyl, 1-propenyl, allyl, isopropenyl, 1-butenyl, 2-butenyl, 1-pentenyl, 2-pentenyl, 2-methyl-2-butenyl, 1-hexenyl, 2-hexenyl, 3-hexenyl, 4-methyl-1-pentenyl, 2-methyl-1-pentenyl, 2-methyl-2-pentenyl, 3-methyl-2-pentenyl, 2,3-dimethyl-2-butenyl, 3,3-dimethyl-1-butenyl, 1-heptenyl, 2-heptenyl, 4-methyl-1-hexenyl, 2,4-dimethyl-1-pentenyl, 2-propyl-1-butenyl, 2,3,3-trimethyl-1-butenyl, 1-octenyl, 2-octenyl, 4-octenyl, 2,4,4-trimethyl-1-pentenyl, 1-nonenyl, 2,3-diethyl-2-pentenyl, 1-decenyl, 5-decenyl, 3-isopropyl-3-heptenyl, 4-undecenyl, 1-dodecenyl, 2-methyl-1-undecenyl, 2,2,4,6,6-pentamethyl-3-heptenyl, 1-tridecenyl, 3-tetradecenyl, 5-pentadecenyl, 1-hexadecenyl, 1,5-dimethyl-2-ethyl-3-propyl-4-nonenyl, 1-octadecenyl, 1,3-butadienyl, 1,3-pentadienyl, 1,4-pentadienyl, 2-methyl-1,3-butadienyl, 3-methyl-1,2-butadienyl, 1,2-hexadienyl, 1,4-hexadienyl, 1,5-hexadienyl, 2,4-hexadienyl, 2-ethyl-1,3-butadienyl, 2-methyl-1,3-pentadienyl, 4-methyl-1,3-pentadienyl, 2,3-dimethyl-1,3-butadienyl, 1,4-heptadienyl, 1,6-heptadienyl, 2,4-dimethyl-1,3-pentadienyl, 1,7-octadienyl, 2,5-dimethyl-2,4-hexadienyl, 1,8-nonadienyl, 7-methyl-2,4-octadienyl, 1,3-decadienyl, 2,6-dimethyl-2,6-octadienyl, 1,10-undecadienyl, 5,6-dimethyl-4-ethyl-1,2-heptadienyl, 1,5-dodecadienyl, 1,12-tridecadienyl, 4-isopropyl-1,9-decadienyl, 6,8-tetradecadienyl, 6,9-pentadecadienyl, 1,15-hexadecadienyl, 6,10-hexadecadienyl, 2,3,11-trimethyl-6,9-tridecadienyl, 7,10-heptadecadienyl, 1,17-octadecadienyl, 2-methyl-7,10-heptadecadienyl, and the like.

The term "$C_1$–$C_3$ alkyl" includes methyl, ethyl, propyl, and isopropyl. Thus, the phrase "$C_3$–$C_{12}$ cycloalkyl, optionally substituted with either one or two $C_1$–$C_3$ alkyl groups" is meant to include, among others, such groups as cyclopropyl, 2-ethylcyclopropyl, cyclobutyl, 2,3-dimethylcyclobutyl, cyclopentyl, 3-propylcyclopentyl, cyclohexyl, 2-methyl-4-isopropylcyclohexyl, cycloheptyl, 3-ethylcycloheptyl, cyclooctyl, cyclononyl, 3,5-diisopropylcyclononyl, cyclodecyl, cycloundecyl, 1-methyl-4-ethylcyclodecyl, cyclododecyl, and the like.

The phrases "$C_5$–$C_{12}$ cycloalkenyl, optionally substituted . . . " and "$C_6$–$C_{12}$ cycloalkadienyl, optionally substituted . . . " are meant to include, among others, such groups as cyclopentenyl, 2-ethylcyclopentenyl, cyclohexenyl, 4-methylcyclohexenyl, 2-isopropyl-5-methylcyclohexenyl, cycloheptenyl, cyclooctenyl, 3,5-dimethylcyclooctenyl, cyclononenyl, 2-ethylcyclononenyl, cyclodecenyl, 4-isopropyl-7-methylcyclodecenyl, cycloundecenyl, 5-methylcycloundecenyl, cyclododecenyl, 3-propylcyclododecenyl, 1,3-cyclohexadienyl, 5-methyl-1,3-cyclohexadienyl, 1,4-cyclohexadienyl, 1,3-cycloheptadienyl, 2,4-dimethyl-1,3-cycloheptadienyl, 2,4-cycloheptadienyl, 1,3-cyclooctadienyl, 1,4-cyclooctadienyl, 1,5-cyclooctadienyl, 1-methyl-2,5-cyclooctadienyl, 1,4-cyclononadienyl, 3,6-dipropyl-1,3-cyclononadienyl, 1,3-cyclodecadienyl, 3-ethyl-1,5-cyclodecadienyl, 2,6-cycloundecadienyl, 4-ethyl-5-methyl-1,7-cycloundecadienyl, 1,3-cyclododecadienyl, 1,7-cyclododecadienyl, 3-propyl-2,5-cyclododecadienyl, and the like.

The term "$C_1$–$C_6$ alkyl" and the alkyl moiety in the terms "$C_1$–$C_6$ alkylthio" and "$C_1$–$C_6$ alkoxy" include methyl, ethyl, propyl, isopropyl, butyl, isobutyl, sec-butyl, t-butyl, pentyl, isopentyl, 1-methylbutyl, 1-ethylpropyl, neopentyl, hexyl, isohexyl, and the like. Accordingly, the phrase "phenyl, optionally substituted . . ." is meant to include, among others, such groups as phenyl, m-tolyl, o-cumenyl, 4-hexylphenyl, 3-trifluoromethylphenyl, 3-isobutylthiophenyl, 2-ethoxyphenyl, 2-fluorophenyl, 3-chlorophenyl, 4-bromophenyl, 3-iodophenyl, 4-cyanophenyl, 2,6-xylyl, 2,4-bis(trifluoromethyl)phenyl, 2-methylthio-4-butylthiophenyl, 2,3-dimethoxyphenyl, 3,5-dichlorophenyl, 2-bromo-5-chlorophenyl, 3,4-dicyanophenyl, 3-trifluoromethyl-5-neopentylphenyl, 5-fluoro-2-methoxyphenyl, mesityl, 4-bromo-3,5-dimethylphenyl, 2-methyl-4-cyano-5-pentylphenyl, 2,5-dichloro-4-fluorophenyl, 2,4,6-triethoxyphenyl, and the like.

The phrase "(cycloalkyl)alkyl, containing . . . " includes, among others, cyclopropylmethyl, 6-(2-ethylcyclopropyl)hexyl, 2,3-dimethylcyclobutylmethyl, 7-cyclopentyl-2,2-dimethyloctyl, cyclohexylmethyl, 3-(3-isopropylcyclohexyl)propyl, 2-(1-methyl-4-ethylcyclooctyl)ethyl, 4-cycloundecylpentyl, and the like.

The phrases "phenylalkyl, containing . . . " and "diphenylalkyl, containing . . . " include, among others, benzyl, phenethyl, 4-(o-cumenyl)octyl, 3-(2-methyl-4-isohexyloxyphenyl)butyl, 1,3-dimethyl-6-(2-cyano-3-ethyl-5-fluorophenyl)heptyl, diphenylmethyl, 2-methyl-2-(m-tolyl)-3-(2,4-dichlorophenyl)propyl, and the like.

It will be understood that the present invention is not to be limited by the exemplification given herein. Various classes of compounds are contemplated, and such various classes of compounds can be employed in either the methods or the insecticidal composition of the present invention. By way of illustration only, each numbered subparagraph below describes an independent class of compounds; in each class, the variables have the general meanings already given if not otherwise stated. Compounds wherein:

1. $R^1$ represents alkyl;
2. $R^1$ represents alkenyl;
3. $R^1$ represents alkadienyl;
4. $R^1$ represents cycloalkyl or substituted cycloalkyl;
5. $R^1$ represents cycloalkenyl or substituted cycloalkenyl;
6. $R^1$ represents cycloalkadienyl or substituted cycloalkadienyl;
7. $R^1$ represents phenyl or substituted phenyl;
8. $R^1$ represents (cycloalkyl)alkyl or (substituted cycloalkyl)alkyl;
9. $R^1$ represents phenylalkyl or (substituted phenyl)alkyl;
10. $R^1$ represents diphenylalkyl, phenyl(substituted phenyl)alkyl, or di(substituted phenyl)alkyl;
11. $R^1$ represents pyridyl, substituted pyridyl, piperidino, substituted piperidino, morpholino, pyrazinyl, or substituted pyrazinyl;
12. $R^1$ represents pyridylalkyl, (substituted pyridyl)alkyl, piperidinoalkyl, (substituted piperidino)alkyl, morpholinoalkyl, pyrazinylalkyl, (substituted pyrazinyl)alkyl, or tetrahydrofurylalkyl;
13. $R^1$ represents alkylamino;
14. $R^1$ represents phenylamino or (substituted phenyl)amino;
15. $R^1$ represents phenyl, optionally monosubstituted with $C_1$–$C_3$ alkyl, $C_1$–$C_4$ alkoxy, chloro, or trifluoromethyl; cycloalkyl; diphenylalkyl; phenylamino; or 3-pyridyl;
16. $R^1$ represents phenyl, optionally monosubstituted with $C_1$–$C_3$ alkyl or $C_1$–$C_4$ alkoxy in the 2- or 4-position, or trifluoromethyl in the 3- or 4-position; $C_6$–$C_8$ cycloalkyl; or diphenylmethyl;
17. $R^1$ represents phenyl;
18. $R^1$ represents 2-methylphenyl, 2-ethylphenyl, or 4-ethylphenyl;
19. $R^1$ represents 4-methoxyphenyl, 4-ethoxyphenyl, or 4-isopropoxyphenyl;
20. $R^1$ represents 3-trifluoromethylphenyl or 4-trifluoromethylphenyl;
21. $R^1$ represents 2-chlorophenyl or 4-chlorophenyl;
22. $R^1$ represents cyclohexyl or cyclooctyl;
23. $R^1$ represents diphenylmethyl;
24. $R^1$ represents phenylamino;
25. $R^1$ represents 3-pyridyl;
26. $R^2$ represents hydrogen, $C_1$–$C_3$ alkyl, or phenyl;
27. $R^2$ represents hydrogen or $C_1$–$C_3$ alkyl;
28. $R^2$ represents hydrogen or methyl;
29. $R^2$ represents methyl;
30. $R^3$ represents hydrogen, $C_1$–$C_3$ alkyl, or phenyl;
31. $R^3$ represents hydrogen or $C_1$–$C_3$ alkyl;
32. $R^3$ represents hydrogen or methyl;
33. $R^3$ represents hydrogen;
34. $R^4$ represents hydrogen or $C_1$–$C_3$ alkyl;
35. $R^4$ represents hydrogen, methyl, or ethyl;
36. $R^4$ represents hydrogen or methyl;
37. $R^4$ represents hydrogen;
38. $R^4$ represents methyl;
39. $R^5$ represents halo, trifluoromethyl, cyano, or 1,1,2,2-tetrafluoroethoxy;
40. $R^5$ represents chloro, bromo, or trifluoromethyl;
41. $R^5$ represents chloro;
42. $R^6$ represents hydrogen, halo, or $C_1$–$C_3$ alkyl;
43. $R^6$ represents hydrogen;
44. The variables are as described in subparagraphs 15 and 27;
45. The variables are as described in subparagraphs 15 and 28;
46. The variables are as described in subparagraphs 15 and 29;
47. The variables are as described in subparagraphs 15 and 31;
48. The variables are as described in subparagraphs 15 and 32;
49. The variables are as described in subparagraphs 15 and 33;
50. The variables are as described in subparagraphs 15 and 35;
51. The variables are as described in subparagraphs 15 and 36;
52. The variables are as described in subparagraphs 15 and 37;
53. The variables are as described in subparagraphs 15 and 38;
54. The variables are as described in subparagraphs 15 and 40;
55. The variables are as described in subparagraphs 15 and 41;
56. The variables are as described in subparagraphs 15 and 43;

57. The variables are as described in subparagraphs 16 and 28;
58. The variables are as described in subparagraphs 16 and 29;
59. The variables are as described in subparagraphs 16 and 32;
60. The variables are as described in subparagraphs 16 and 33;
61. The variables are as described in subparagraphs 16 and 36;
62. The variables are as described in subparagraphs 16 and 37;
63. The variables are as described in subparagraphs 16 and 38;
64. The variables are as described in subparagraphs 16 and 41;
65. The variables are as described in subparagraphs 16 and 43;
66. The variables are as described in subparagraphs 15, 27, and 31;
67. The variables are as described in subparagraphs 15, 27, and 32;
68. The variables are as described in subparagraphs 15, 27, and 33;
69. The variables are as described in subparagraphs 15, 27, and 35;
70. The variables are as described in subparagraphs 15, 27, and 36;
71. The variables are as described in subparagraphs 15, 27, and 37;
72. The variables are as described in subparagraphs 15, 27, and 38;
73. The variables are as described in subparagraphs 15, 27, and 40;
74. The variables are as described in subparagraphs 15, 27, and 41;
75. The variables are as described in subparagraphs 15, 27, and 43;
76. The variables are as described in subparagraphs 15, 28, and 31;
77. The variables are as described in subparagraphs 15, 28, and 32;
78. The variables are as described in subparagraphs 15, 28, and 33;
79. The variables are as described in subparagraphs 15, 28, and 35;
80. The variables are as described in subparagraphs 15, 28, and 36;
81. The variables are as described in subparagraphs 15, 28, and 37;
82. The variables are as described in subparagraphs 15, 28, and 38;
83. The variables are as described in subparagraphs 15, 28, and 40;
84. The variables are as described in subparagraphs 15, 28, and 41;
85. The variables are as described in subparagraphs 15, 28, and 43;
86. The variables are as described in subparagraphs 15, 29, and 31;
87. The variables are as described in subparagraphs 15, 29, and 32;
88. The variables are as described in subparagraphs 15, 29, and 33;
89. The variables are as described in subparagraphs 15, 29, and 35;
90. The variables are as described in subparagraphs 15, 29, and 36;
91. The variables are as described in subparagraphs 15, 29, and 37;
92. The variables are as described in subparagraphs 15, 29, and 38;
93. The variables are as described in subparagraphs 15, 29, and 40;
94. The variables are as described in subparagraphs 15, 29, and 41;
95. The variables are as described in subparagraphs 15, 29, and 43;
96. The variables are as described in subparagraphs 16, 28, and 32;
97. The variables are as described in subparagraphs 16, 28, and 33;
98. The variables are as described in subparagraphs 16, 28, and 36;
99. The variables are as described in subparagraphs 16, 28, and 37;
100. The variables are as described in subparagraphs 16, 28, and 38;
101. The variables are as described in subparagraphs 16, 28, and 41;
102. The variables are as described in subparagraphs 16, 28, and 43;
103. The variables are as described in subparagraphs 16, 29, and 32;
104. The variables are as described in subparagraphs 16, 29, and 33;
105. The variables are as described in subparagraphs 16, 29, and 36;
106. The variables are as described in subparagraphs 16, 29, and 37;
107. The variables are as described in subparagraphs 16, 29, and 38;
108. The variables are as described in subparagraphs 16, 29, and 41;
109. The variables are as described in subparagraphs 16, 29, and 43;
110. The variables are as described in subparagraphs 15, 27, 31, 35, and 43;
111. The variables are as described in subparagraphs 15, 27, 31, 36, and 43;
112. The variables are as described in subparagraphs 15, 27, 31, 37, and 43;
113. The variables are as described in subparagraphs 15, 28, 31, 35, and 43;
114. The variables are as described in subparagraphs 15, 28, 31, 36, and 43;
115. The variables are as described in subparagraphs 15, 28, 31, 37, and 43;
116. The variables are as described in subparagraphs 15, 29, 31, 35, and 43;
117. The variables are as described in subparagraphs 15, 29, 31, 36, and 43;
118. The variables are as described in subparagraphs 15, 29, 31, 37, and 43;
119. The variables are as described in subparagraphs 15, 27, 32, 35, and 43;
120. The variables are as described in subparagraphs 15, 27, 32, 36, and 43;
121. The variables are as described in subparagraphs 15, 27, 32, 37, and 43;
122. The variables are as described in subparagraphs 15, 28, 32, 35, and 43;
123. The variables are as described in subparagraphs 15, 28, 32, 36, and 43;
124. The variables are as described in subparagraphs 15, 28, 32, 37, and 43;

125. The variables are as described in subparagraphs 15, 29, 32, 35, and 43;
126. The variables are as described in subparagraphs 15, 29, 32, 36, and 43;
127. The variables are as described in subparagraphs 15, 29, 32, 37, and 43;
128. The variables are as described in subparagraphs 15, 27, 33, 35, and 43;
129. The variables are as described in subparagraphs 15, 27, 33, 36, and 43;
130. The variables are as described in subparagraphs 15, 27, 33, 37, and 43;
131. The variables are as described in subparagraphs 15, 28, 33, 35, and 43;
132. The variables are as described in subparagraphs 15, 28, 33, 36, and 43;
133. The variables are as described in subparagraphs 15, 28, 33, 37, and 43;
134. The variables are as described in subparagraphs 15, 29, 33, 35, and 43;
135. The variables are as described in subparagraphs 15, 29, 33, 36, and 43;
136. The variables are as described in subparagraphs 15, 29, 33, 37, and 43;
137. The variables are as described in subparagraphs 16, 28, 32, 35, and 43;
138. The variables are as described in subparagraphs 16, 28, 32, 36, and 43;
139. The variables are as described in subparagraphs 16, 28, 32, 37, and 43;
140. The variables are as described in subparagraphs 16, 28, 33, 35, and 43;
141. The variables are as described in subparagraphs 16, 28, 33, 36, and 43;
142. The variables are as described in subparagraphs 16, 28, 33, 37, and 43;
143. The variables are as described in subparagraphs 16, 29, 32, 35, and 43;
144. The variables are as described in subparagraphs 16, 29, 32, 36, and 43;
145. The variables are as described in subparagraphs 16, 29, 32, 37, and 43;
146. The variables are as described in subparagraphs 16, 29, 33, 35, and 43;
147. The variables are as described in subparagraphs 16, 29, 33, 36, and 43;
148. The variables are as described in subparagraphs 16, 29, 33, 37, and 43;
149. The variables are as described in subparagraphs 17, 28, 33, 37, 41, and 43;
150. The variables are as described in subparagraphs 17, 28, 33, 37, 40, and 43;
151. The variables are as described in subparagraphs 17, 29, 33, 36, 41, and 43;
152. The variables are as described in subparagraphs 17, 29, 33, 37, 41, and 43;
153. The variables are as described in subparagraphs 18, 28, 33, 37, 41, and 43;
154. The variables are as described in subparagraphs 18, 29, 33, 37, 41, and 43;
155. The variables are as described in subparagraphs 19, 28, 33, 37, 41, and 43;
156. The variables are as described in subparagraphs 19, 29, 33, 37, 41, and 43;
157. The variables are as described in subparagraphs 20, 28, 33, 37, 40, and 43;
158. The variables are as described in subparagraphs 20, 29, 33, 37, 41, and 43;
159. The variables are as described in subparagraphs 22, 28, 33, 37, 41, and 43;
160. The variables are as described in subparagraphs 23, 29, 33, 37, 41, and 43; and
161. The variables are as described in subparagraphs 25, 29, 33, 37, 41, and 43.

It should be apparent from the foregoing that any and all possible combinations of variables are within the scope of the present invention. From the above examples of contemplated classes, it is possible for one having ordinary skill in the art to construct any desired class, whether specifically exemplified or not. Thus, the present invention consists of multiple subgenera, with each subgenus consisting of a contemplated class of compounds as illustrated above without being limited thereto. Stated differently, any subgenus not specifically set forth herein is still implicitly within the scope of the present invention.

In order to further clarify the present invention, the following list of compounds is given by way of illustration. It is to be understood, however, that the present invention is neither confined to nor limited by the compounds listed.

1. 2-(5-methylhexylimino)-4-methyl-5-phenyl-N-[3-(1,1,2,2-tetrafluoroethoxy)phenyl]-3-thiazolidinecarbothioamide,
2. 4-ethyl-N-(3-iodo-5-methylphenyl)-2-(3,5,10-trimethyltridecylimino)-3-thiazolidinecarbothioamide,
3. N-(3-bromophenyl)-2-vinylimino-3-thiazolidinecarbothioamide,
4. N-(3-cyanophenyl)-5-methyl-2-isopropenylimino-3-thiazolidinecarbothioamide,
5. 2-(2-methyl-2-butenylimino)-4-methyl-5-phenyl-N-[3-(1,1,2,2-tetrafluoroethoxy)phenyl]-3-thiazolidinecarbothioamide,
6. N-(3-chloro-4-fluorophenyl)-2-(1-octenylimino)-3-thiazolidinecarbothioamide,
7. N-(3-bromophenyl)-4-isopropyl-2-(2,2,4,6,6-pentamethyl-3-heptenylimino)-3-thiazolidinecarbothioamide,
8. N-(3-chlorophenyl)-2-(1,5-dimethyl-2-ethyl-3-propyl-4-nonenylimino)-3-thiazolidinecarbothioamide,
9. N-(3-chlorophenyl)-2-(1-octadecenylimino)-3-thiazolidinecarbothioamide,
10. 2-(1,3-butadienylimino)-4-ethyl-N-(3-iodophenyl)-3-thiazolidinecarbothioamide,
11. N-(3-chlorophenyl)-2-(1,6-heptadienylimino)-3-thiazolidinecarbothioamide,
12. 2-(7-methyl-2,4-octadienylimino)-5-phenyl-N-(3-trifluoromethylphenyl)-3-thiazolidinecarbothioamide,
13. N-(3-fluorophenyl)-2-(6,8-tetradecadienylimino)-3-thiazolidinecarbothioamide,
14. N-(3-cyano-4-ethylphenyl)-4-methyl-2-(2-methyl-7,10-heptadecadienylimino)-3-thiazolidinecarbothioamide,
15. N-(3-cyanophenyl)-4-ethyl-2-(3-methyl-5-ethylcycloundecylimino)-3-thiazolidinecarbothioamide,
16. N-(3-chlorophenyl)-2-(2-ethyl-2-cyclopentenylimino)-3-thiazolidinecarbothioamide.
17. N-(3-cyanophenyl)-2-(1-cyclohexenylimino)-4,5-diethyl-3-thiazolidinecarbothioamide,
18. N-(3-chlorophenyl)-2-(3-isopropyl-5-methyl-2-cyclohexenylimino)-3-thiazolidinecarbothioamide,
19. N-(3-chlorophenyl)-5-phenyl-2-(4-cyclononenylimino)-3-thiazolidinecarbothioamide,
20. 2-(3-propyl-5-cyclododecenylimino)-N-[3-(1,1,2,2-tetrafluoroethoxy)phenyl]-3-thiazolidinecarbothioamide, 21. N-(3-bromo-6-propylphenyl)-2-(1,3-cyclohexadienylimino)-3-thiazolidinecarbothioamide, 22. N-(3-chlorophenyl)-2-(3,5-dimethyl-2,4-cycloheptadienylimino)-4-methyl-3-thiazolidinecarbothioamide, 23. 2-(3-ethyl-1,5-cyclodecadienylimino)-N-(3-trifluoromethylphenyl)-3-thiazolidinecarbothioamide, 24. N-(3-chlorophenyl)-2-(1,7-cyclododecadienylimino)-3-thiazolidinecarbothioamide, 25. 2-(2,5-dichloro-3-isohexylphenylimino)-N-(3-iodo-5-fluorophenyl)-3-thiazolidinecarbothioamide, 26. 2-(2,6-dimethoxyphenylimino)-5-propyl-N-(3-trifluoromethylphenyl)-3-thiazolidinecarbothioamide, 27. N-(3-chlorophenyl)-2-(5-cyclopropyl-3-ethylhexylimino)-5,5-dimethyl-3-thiazolidinecarbothioamide, 28. 2-[3-(5-ethylcyclononyl)propylimino]-N-(3-fluorophenyl)-4-methyl-3-thiazolidinecarbothioamide, 29. 2-cyclododecylmethylimino-N-(3-trifluoromethyl-4-ethylphenyl)-4,5,5-trimethyl-3-thiazolidinecarbothioamide, 30. 4-methyl-2-(2-methyl-2-phenylpropylimino)-N-(3-trifluoromethylphenyl)-3-thiazolidinecarbothioamide, 31. N-(3-chlorophenyl)-2-(2-phenyldecylimino)-3-thiazolidinecarbothioamide, 32. N-(3-bromophenyl)-2-[7-(3-ethylthio-4-trifluoromethylphenyl)-2-methylheptylimino]-3-thiazolidinecarbothioamide, 33. 2-[2-(2,4-dimethoxy-5-cyanophenyl)ethylimino]-N-(3-fluorophenyl)-4-methyl-3-thiazolidinecarbothioamide, 34. 5-ethyl-N-(3-trifluoromethylphenyl)-2-[2,2-dimethyl-3-(3-trifluoromethylphenyl)propylimino]-3-thiazolidinecarbothioamide, 35. N-(3-chlorophenyl)-2-(5,5-diphenylpentylimino)-3-thiazolidinecarbothioamide, 36. 4,5-dimethyl-2-(2,4-diphenylbutylimino)-N-(3-iodophenyl)-3-thiazolidinecarbothioamide, 37. 4-isopropyl-2-[1-phenyl-1-(3,5-dibromophenyl)-ethylimino]-N-[3-(1,1,2,2-tetrafluoroethoxy)phenyl]-3-thiazolidinecarbothioamide, 38. N-(3-chlorophenyl)-2-[2-(4-ethylthiophenyl)-3-(2-chloro-4-cyano-5-methylthiophenyl)propylimino]-3-thiazolidinecarbothioamide, 39. N-(3-bromophenyl)-5-ethyl-2-(2-chloro-5-ethoxy-4-pyridylimino)-3-thiazolidinecarbothioamide, 40. 2-(4-ethylpiperidinoimino)-N-(3-fluorophenyl)-5-methyl-3-thiazolidinecarbothioamide, 41. 2-(4-pyridylmethylimino)-N-(3-trifluoromethylphenyl)-3-thiazolidinecarbothioamide, 42. N-(3-chloro-6-methylphenyl)-4,5-dipropyl-2-[4-(3-pyridyl)hexylimino]-3-thiazolidinecarbothioamide, 43. N-(3-chlorophenyl)-5-ethyl-2-[2-(3-isopropoxy-2-pyridyl)propylimino]-3-thiazolidinecarbothioamide, 44. 2-[10-(2-ethyl-3-pyridyl)decylimino]-5-methyl-N-(3-trifluoromethylphenyl)-3-thiazolidinecarbothioamide, 45. N-(3-bromophenyl)-2-piperidinomethylimino-3-thiazolidinecarbothioamide, 46. N-(3-chlorophenyl)-4,5-dimethyl-2-(4-piperidinoundecylimino)-3-thiazolidinecarbothioamide, 47. N-(3-bromophenyl)-2-[2-(2,3-dimethyl-piperidino)-ethylimino]-3-thiazolidinecarbothioamide, 48. 2-[2-ethyl-3-(4-propylpiperidino)hexylimino]-4-methyl-N-[3-(1,1,2,2-tetrafluoroethoxy)phenyl]-3-thiazolidinecarbothioamide, 49. N-(3-chlorophenyl)-4-ethyl-2-[7-(4-isopropylpiperidino)nonylimino]-3-thiazolidinecarbothioamide, 50. N-(3-bromophenyl)-2-(3-morpholinopropylimino)-3-thiazolidinecarbothioamide, 51. 2-(3-ethyl-7,7-dimethyl-5-morpholinooctylimino)-5-methyl-N-(3-trifluoromethylphenyl)-3-thiazolidinecarbothioamide, 52. N-(3-cyanophenyl)-2-[1-methyl-2-(3-isopropyl-2-pyrazinyl)ethylimino]-3-thiazolidinecarbothioamide, 53. N-(3-chlorophenyl)-4-methyl-2-[9-(2-pyrazinyl)-nonylimino]-3-thiazolidinecarbothioamide, 54. 2-[2-ethyl-4-(3-tetrahydrofuryl)hexylimino]-N-(3-fluorophenyl)-3-thiazolidinecarbothioamide, 55. N-(3-iodophenyl)-5-propyl-2-[13-(2-tetrahydrofuryl)tridecylimino]-3-thiazolidinecarbothioamide, 56. 2-dodecylhydrazono-5-isopropyl-N-(3-trifluoromethylphenyl)-3-thiazolidinecarbothioamide, 57. N-(3-bromophenyl)-2-dimethylhydrazono-5-ethyl-5-methyl-4-propyl-3-thiazolidinecarbothioamide, 58. N-(3-cyanophenyl)-2-(3-methoxyphenylhydrazono)-5-methyl-3-thiazolidinecarbothioamide, 59. N-(3-chlorophenyl)-2-[(phenyl) (2,3-dibromophenyl)hydrazono]-3-thiazolidinecarbothioamide, 60. 4-methyl-2-[(hexyl) (phenyl)hydrazono]-N-[3-(1,1,2,2-tetrafluoroethoxy)phenyl]-3-thiazolidinecarbothioamide, 61. N-(3-cyanophenyl)-2-phenethylhydrazono-3-thiazolidinecarbothioamide, 62. N-(3-chlorophenyl)-2-{[2-methyl-3-(4-ethylphenyl)propyl](7-phenyldodecyl)hydrazono}-3-thiazolidinecarbothioamide, 63. 2-[(benzyl) (3-isopropylthiophenyl)hydrazono]-N-(3-fluorophenyl)-5-methyl-3-thiazolidinecarbothioamide, and 64. N-(3-chlorophenyl)-2-[(2-ethyloctyl) (2-phenylpentyl)hydrazono]-3-thiazolidinecarbothioamide.

The compounds of the present invention are prepared in accordance with methods well known to those having ordinary skill in the art. In general, the compounds can be prepared by reacting an appropriately-substituted 2-amino-2-thiazoline with an equivalent amount of a suitably-substituted phenyl isothiocyanate, as shown by the following equation:

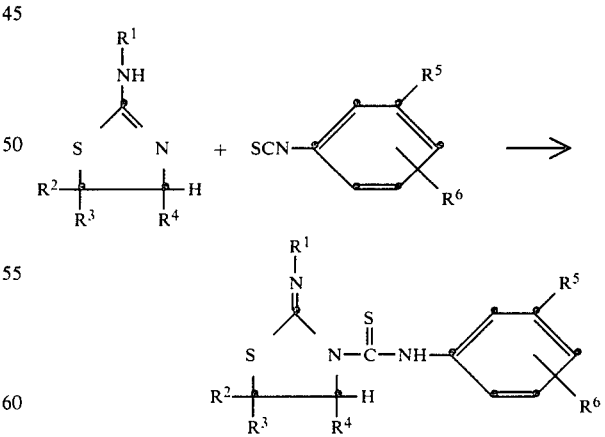

wherein the variables are as defined hereinbefore. The reaction typically is carried out at ambient temperature for approximately 14 hours in a suitable solvent. If desired, shorter reaction times will result by heating the reaction mixture at an elevated temperature, up to and including the reflux temperature of the reaction mixture. Furthermore, the reaction can be carried out in the presence of a catalytic amount of a tertiary amine, such as triethylamine or triethylenediamine. Suitable solvents include, among others, benzene, toluene, the xylenes, chloroform, ethyl acetate, acetonitrile, and the like. Chloroform is the solvent of choice. The reaction mixture then is worked up in accordance with the usual procedures. Typically, the solvent is removed under reduced pressure and the residue recrystallized from a suitable solvent or solvent combination. The most frequently used recrystallization solvents and solvent combinations are benzene, hexane, benzene/hexane, chloroform/hexane, ethyl acetate/hexane, ethanol, and aqueous ethanol.

An alternate route to the compounds of the present invention is available in those instances where the substituent on the 2-imino nitrogen and the substituent on the carbothioamide nitrogen are the same. This alternative procedure involves simply reacting two equivalents of the desired phenyl isothiocyanate with one equivalent of a 2-haloethylamine, such as a 2-chloro- or 2-bromoethylamine. The reaction is carried out in a suitable solvent such as chloroform and in the presence of a suitable base, such as triethylamine or sodium carbonate. Normally, the reaction is carried out at ambient temperature. The product then is isolated in accordance with known procedures.

The phenyl isothiocyanate starting materials are readily prepared by known methods from the corresponding amines (anilines). For example, the appropriately-substituted amine is reacted with N,N-dimethylthiocarbamoyl chloride in a suitable solvent, such as benzene, toluene, or a xylene. Typically, the reaction is carried out at reflux temperature for approximately 14 hours. The resulting phenyl isothiocyanate normally is isolated and purified by distillation. Alternatively, the appropriately-substituted aniline can be reacted with thiophosgene in chloroform in the presence of aqueous sodium carbonate at a temperature of 10°–15° C.

The 2-amino-2-thiazoline starting materials also are prepared in accordance with known procedures. In general, a 2-thiazoline is obtained upon cyclizing an appropriately-substituted 1-allyl- or 1-(2-hydroxyethyl)thiourea in the presence of heat and 6 N hydrochloric acid, as shown by the following equation:

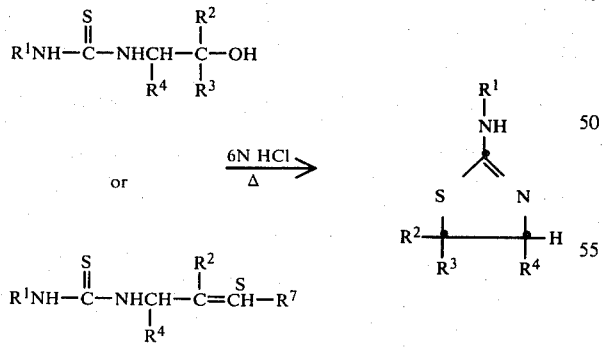

wherein $R^7$ together with the carbon atom to which it is attached give $R^3$ upon cyclization and the other variables are as defined hereinbefore.

The 1-(2-hydroxyethyl)thioureas typically are obtained by reacting a phenyl isothiocyanate with a 2-aminoethanol in chloroform at ambient temperature. Under such conditions, the resulting thiourea is insoluble and separates from the reaction mixture as a relatively pure crystalline product. Accordingly, the hydroxyethylthioureas are the preferred intermediates to the preparation of the required 2-thiazolines. The 1-allylthioureas in general are prepared by reacting an appropriately-substituted aniline with an appropriately-substituted allyl isothiocyanate, again at room temperature and in a suitable solvent such as chloroform. The resulting thiourea typically is purified by chromatographing the reaction mixture on a silica gel column, using as eluant a toluene/ethyl acetate mixture. As already indicated, the hydroxyethylthioureas are the preferred intermediates; however, either type of intermediate can be employed to prepare any one of the compounds of the present invention.

The examples which follow illustrate the preparations of representative compounds of the present invention. In each case, the compound was identified by elemental microanalysis and nuclear magnetic resonance analysis. Unless stated otherwise, all temperatures are given in degrees Celsius.

EXAMPLE 1

Preparation of N-(3-chlorophenyl)-5-methyl-2-methylimino-3-thiazolidinecarbothioamide A mixture of 2.6 g. of 2-methylamino-5-methyl-2-thiazoline and 3.4 g. of m-chlorophenyl isothiocyanate in approximately 75 ml. of chloroform was stirred for about 14 hours at ambient temperature. The solvent was distilled under reduced pressure and the residue was recrystallized from ethanol. The resulting product melted at 106°–8°. Since nuclear magnetic resonance analysis indicated the presence of approximately 10% of an impurity, the material was recrystallized from benzene/hexane, giving 1.0 g. (17%) of N-(3-chlorophenyl)-5-methyl-2-methylimino-3-thiazolidinecarbothioamide. The following elemental microanalysis was obtained:

Calculated for $C_{12}H_{14}ClN_3S_2$: C, 48.07; H, 4.71; N, 14.01. Found: C, 48.05; H, 4.64; N, 13.72.

Each of the following compounds was prepared in accordance with the general procedure of Example 1, using the appropriately-substituted 2-amino-2-thiazoline and phenyl isothiocyanate. When available, the percent yield, melting point, recrystallization solvent, and elemental microanalysis are given for each compound.

EXAMPLE 2

N-(3-Chlorophenyl)-2-isopropylimino-5-methyl-3-thiazolidinecarbothioamide, 30%, 49°–50°, aqueous ethanol.

Calculated for $C_{14}H_{18}ClN_3S_2$: C, 51.28; H, 5.53; N, 12.81. Found: C, 51.09; H, 5.80; N, 12.74.

EXAMPLE 3

2-Butylimino-N-(3-chlorophenyl)-5-methyl-3-thiazolidinecarbothioamide, 10%, 55°–60°, ethanol.

Calculated for $C_{15}H_{20}ClN_3S_2$: C, 52.69; H, 5.90; N, 12.29. Found: C, 52.69; H, 5.91; N, 12.43.

EXAMPLE 4

N-(3-Chlorophenyl)-2-decylimino-5-methyl-3-thiazolidinecarbothioamide, 26%, 34°–6°, ethanol.

Calculated for $C_{21}H_{32}ClN_3S_2$: C, 59.20; H, 7.57; N, 9.86. Found: C, 58.96; H, 7.66; N, 9.86.

EXAMPLE 5

N-(3-Chlorophenyl)-5-methyl-2-undecylimino-3-thiazolidinecarbothioamide, 29%, 42°–4°, hexane.

Calculated for $C_{22}H_{34}ClN_3S_2$: C, 60.04; H, 7.79; N, 9.55. Found: C, 59.81; H, 7.58; N, 9.60.

EXAMPLE 6

N-(3-Chlorophenyl)-2-dodecylimino-5-methyl-3-thiazolidinecarbothioamide, 53%, 47°–9°, ethanol.

Calculated for $C_{23}H_{36}ClN_3S_2$: C, 60.83; H, 7.99; N, 9.25. Found: C, 61.06; H, 7.91; N, 9.14.

EXAMPLE 7

N-(3-Chlorophenyl)-5-methyl-2-octadecylimino-3-thiazolidinecarbothioamide, 50%, 65°–6°, aqueous ethanol.

Calculated for $C_{29}H_{48}ClN_3S_2$: C, 64.71; H, 8.99; N, 7.81. Found: C, 64.64; H, 8.41; N, 7.75.

EXAMPLE 8

2-Allylimino-N-(3-chlorophenyl)-3-thiazolidinecarbothioamide, ethanol.

Calculated for $C_{13}H_{14}ClN_3S_2$: C, 50.07; H, 4.53; N, 13.47. Found: C, 49.97; H, 4.33; N, 13.22.

EXAMPLE 9

N-(3-Chlorophenyl)-2-cyclopropylimino-5-methyl-3-thiazolidinecarbothioamide, 41%, 91°–3°, benzene/hexane/ethanol Calculated for $C_{14}H_{16}ClN_3S_2$: C, 51.60; H, 4.95; N, 12.89. Found: C, 51.89; H, 5.17; N, 13.08.

EXAMPLE 10

N-(3-Chlorophenyl)-2-cyclopentylimino-5-methyl3-thiazolidinecarbothioamide, 18%, 75°–7°, aqueous ethanol Calculated for $C_{16}H_{20}ClN_3S_2$: C, 54.31; H, 5.66; N, 11.88. Found: C, 54.14; H, 6.10; N, 11.79.

EXAMPLE 11

2-Cyclohexylimino-N-(3-fluorophenyl)-3-thiazolidinecarbothioamide, 21%, 97°–9°, benzene/hexane The reaction was carried out in the presence of a catalytic amount of triethylenediamine.

Calculated for $C_{16}H_{20}FN_3S_2$: C, 56.94; H, 5.97; N, 12.45. Found: C, 56.89; H, 5.80; N, 12.24.

EXAMPLE 12

N-(3-Chlorophenyl)-2-cyclohexylimino-3-thiazolidinecarbothioamide, 20%, 106°–8°, aqueous ethanol Calculated for $C_{16}H_{20}ClN_3S_2$: C, 54.30; H, 5.70; N, 11.87. Found: C, 54.32; H, 5.46; N, 11.63.

EXAMPLE 13

N-(3-Chlorophenyl)-5-methyl-2-(2-methylcyclohexylimino)-3-thiazolidinecarbothioamide, 10%, oil, hexane. The product was approximately 75% pure.

EXAMPLE 14

2-(4-t-Butylcyclohexylimino)-N-(3-chlorophenyl)-5-methyl-3-thiazolidinecarbothioamide, 40%, 121°–3°, ethanol Calculated for $C_{21}H_{30}ClN_3S_2$: C, 59.48; H, 7.13; N, 9.91. Found: C, 59.77; H, 6.82; N, 9.68.

EXAMPLE 15

N-(3-Chlorophenyl)-2-cycloheptylimino-5-methyl-thiazolidinecarbothioamide, 47%, 62°–4°, hexane Calculated for $C_{18}H_{24}ClN_3S_2$: C, 56.60; H, 6.33; N, 11.00. Found: C, 56.87; H, 6.51; N, 11.26.

EXAMPLE 16

N-(3-Chlorophenyl)-2-cyclooctylimino-5-methyl-3-thiazolidinecarbothioamide, 20%, 76°–7°, ethanol Calculated for $C_{19}H_{26}ClN_3S_2$: C, 57.63; H, 6.62; N, 10.61. Found: C, 57.64; H, 6.86; N, 10.79.

EXAMPLE 17

N-(3-Fluorophenyl)-2-phenylimino-3-thiazolidinecarbothioamide, 46%, 119°–21°, benzene/hexane Calculated for $C_{16}H_{14}FN_3S_2$: C, 57.98; H, 4.26; N, 12.68. Found: C, 57.72; H, 4.31; N, 12.41.

EXAMPLE 18

N-(3-Chlorophenyl)-2-phenylimino-3-thiazolidinecarbothioamide, 52%, 99°–101°, benzene/hexane The reaction was carried out in the presence of a catalytic amount of triethylenediamine Calculated for $C_{16}H_{14}ClN_3S_2$: C, 55.24; H, 4.06; N, 12.08. Found: C, 55.48; H, 4.26; N, 12.05.

EXAMPLE 19

N-(3-Bromophenyl)-2-phenylimino-3-thiazolidinecarbothioamide, 25%, 114°–6°, benzene The reaction was carried out in the presence of a catalytic amount of triethylenediamine Calculated for $C_{16}H_{14}BrN_3S_2$: C, 48.98; H, 3.60; N, 10.71. Found: C, 48.75; H, 3.82; N, 10.42.

EXAMPLE 20

N-(3-Iodophenyl)-2-phenylimino-3-thiazolidinecarbothioamide, 5%, 134°–6°, aqueous ethanol Calculated for $C_{16}H_{14}IN_3S_2$: C, 43.74; H, 3.21; N, 9.56. Found: C, 43.93; H, 3.37; N, 9.83.

EXAMPLE 21

2-Phenylimino-N-(3-trifluoromethylphenyl)-3-thiazolidinecarbothioamide, 30%, 100°–2°, benzene/hexane Calculated for $C_{17}H_{14}F_3N_3S_2$: C, 53.53; H, 3.70; N, 11.02. Found: C, 53.24; H, 3.71; N, 10.91.

EXAMPLE 22

N-(3-Cyanophenyl)-2-phenylimino-3-thiazolidinecarbothioamide, 38%, 120°-2°, benzene Calculated for $C_{17}H_{14}N_4S_2$: C, 60.33; H, 4.17; N, 16.55. Found: C, 60.07; H, 4.09; N, 16.27.

EXAMPLE 23

2-Phenylimino-N-[3-(1,1,2,2-tetrafluoroethoxy)phenyl]-3-thiazolidinecarbothioamide, 19%, 72°-4°, aqueous ethanol Calculated for $C_{18}H_{15}F_4N_3OS_2$: C, 50.34; H, 3.52; N, 9.78. Found: C, 50.01; H, 3.61; N, 10.02.

EXAMPLE 24

N-(3,5-Dichlorophenyl)-2-phenylimino-3-thiazolidinecarbothioamide, 24%, 127°-9°, benzene/hexane Calculated for $C_{16}H_{13}Cl_2N_3S_2$: C, 50.26; H, 3.43; N, 10.99. Found: C, 50.42; H, 3.47; N, 10.78.

EXAMPLE 25

N-(3-Chlorophenyl)-5-methyl-2-phenylimino-3-thiazolidinecarbothioamide, 52%, 101°-2°, aqueous ethanol Calculated for $C_{17}H_{16}ClN_3S_2$: C, 56.42; H, 4.46; N, 11.61. Found: C, 56.42; H, 4.50; N, 11.40.

EXAMPLE 26

5-Methyl-2-phenylimino-N-(3-trifluoromethylphenyl)-3-thiazolidinecarbothioamide, 13%, 55°-6°, benzene/hexane Calculated for $C_{18}H_{16}F_3N_3S_2$: C, 54.67; H, 4.08; N, 10.63. Found: C, 54.48; H, 4.00; N, 10.69.

EXAMPLE 27

N-(3-Chlorophenyl)-5-ethyl-2-phenylimino-3-thiazolidinecarbothioamide, 48%, 64°-6°, aqueous ethanol Calculated for $C_{18}H_{18}ClN_3S_2$: C, 57.51; H, 4.83; N, 11.18. Found: C, 57.49; H, 4.69; N, 11.21.

EXAMPLE 28

N-(3-Fluorophenyl)-5-phenyl-2-phenylimino-3-thiazolidinecarbothioamide, 54%, 103°-5°, ethyl acetate/hexane The reaction was carried out in the presence of a catalytic amount of triethylenediamine.

Calculated for $C_{22}H_{18}FN_3S_2$: C, 64.84; H, 4.45; N, 10.31; S, 15.74. Found: C, 64.74; H, 4.26; N, 10.29; S, 15.74.

EXAMPLE 29

N-(3-Chlorophenyl)-4-ethyl-2-phenylimino-3-thiazolidinecarbothioamide, 5%, 120°-2°, aqueous ethanol Calculated for $C_{18}H_{18}ClN_3S_2$: C, 57.51; H, 4.83; N, 11.18. Found: C, 57.30; H, 4.90; N, 11.02.

EXAMPLE 30

N-(3-Chlorophenyl)-5,5-dimethyl-2-phenylimino-3-thiazolidinecarbothioamide, 21%, 150°-2°, benzene/hexane The reaction was carried out in the presence of a catalytic amount of triethylenediamine.

Calculated for $C_{18}H_{18}ClN_3S_2$: C, 57.51; H, 4.83; N, 11.18. Found: C, 57.31; H, 5.07; N, 10.93.

EXAMPLE 31

N-(3-Chlorophenyl)-4,5-dimethyl-2-phenylimino-3-thiazolidinecarbothioamide, 40%, 100°-3°, ethanol Calculated for $C_{18}H_{18}ClN_3S_2$: C, 57.51; H, 4.83; N, 11.18. Found: C, 57.67; H, 4.67; N, 11.10.

EXAMPLE 32

N-(3-Chlorophenyl)-2-o-tolylimino-3-thiazolidinecarbothioamide, 50%, 107°-9°, ethanol Calculated for $C_{17}H_{16}ClN_3S_2$: C, 56.42; H, 4.46; N, 11.61. Found: C, 56.20; H, 4.57; N, 11.69.

EXAMPLE 33

N-(3-Chlorophenyl)-5-methyl-2-o-tolylimino-3-thiazolidinecarbothioamide, 74%, 108°-10°, ethanol Calculated for $C_{18}H_{18}ClN_3S_2$: C, 57.51; H, 4.83; N, 11.18. Found: C, 57.72; H, 5.05; N, 11.44.

EXAMPLE 34

N-(3,4-Dichlorophenyl)-5-methyl-2-o-tolylimino-3-thiazolidinecarbothioamide, 87%, 96°-8°, ethanol Calculated for $C_{18}H_{17}Cl_2N_3S_2$: C, 52.68; H, 4.18; N, 10.24. Found: C, 52.88; H, 4.18; N, 10.35.

EXAMPLE 35

N-(3-Chloro-2-methylphenyl)-5-methyl-2-o-tolylimino-3-thiazolidinecarbothioamide, 93°-5°, ethanol Calculated for $C_{19}H_{20}ClN_3S_2$: C, 58.52; H, 5.17; N, 10.78. Found: C, 58.51; H, 5.13; N, 10.72.

EXAMPLE 36

N-(3-Chloro-6-methylphenyl)-5-methyl-2-o-tolylimino-3-thiazolidinecarbothioamide, 76°-7°, ethanol Calculated for $C_{19}H_{20}ClN_3S_2$: C, 58.52; H, 5.13; N, 10.78. Found: C, 58.31; H, 4.91; N, 10.63.

EXAMPLE 37

N-(3-Chlorophenyl)-5-methyl-2-p-tolylimino-3-thiazolidinecarbothioamide, 37%, 104°-6°, ethanol Calculated for $C_{18}H_{18}ClN_3S_2$: C, 57.51; H, 4.83; N, 11.18. Found: C, 57.32; H, 4.91; N, 11.19.

EXAMPLE 38

N-(3-Chlorophenyl)-2-(2-ethylphenylimino)-3-thiazolidinecarbothioamide, 19%, 116°-7°, aqueous ethanol Calculated for $C_{18}H_{18}ClN_3S_2$: C, 57.51; H, 4.83; N, 11.18. Found: C, 57.36; H, 4.98; N, 11.14.

EXAMPLE 39

N-(3-Chlorophenyl)-2-(2-ethylphenylimino)-5-methyl-3-thiazolidinecarbothioamide, 23%, 79°-80°, ethanol Purification required column chromatography on silica gel with benzene as solvent.

Calculated for $C_{19}H_{20}ClN_3S_2$: C, 58.52; H, 5.13; N, 10.78. Found: C, 58.74; H, 5.25; N, 10.96.

EXAMPLE 40

N-(3-Chlorophenyl)-2-(3-ethylphenylimino)-5-methyl-3-thiazolidinecarbothioamide, 43%, 94°–5°, ethanol Calculated for $C_{19}H_{20}ClN_3S_2$: C, 58.52; H, 5.13; N, 10.78. Found: C, 58.78; H, 5.37; N, 10.98.

EXAMPLE 41

N-(3-Chlorophenyl)-2-(4-ethylphenylimino)-5-methyl-3-thiazolidinecarbothioamide, 7%, 82°–4°, ethanol Calculated for $C_{19}H_{20}ClN_3S_2$: C, 58.52; H, 5.17; N, 10.78. Found: C, 57.38; H, 7.17; N, 10.59.

EXAMPLE 42

N-(3-Chlorophenyl)-2-(4-isopropylphenylimino)-5-methyl-3-thiazolidinecarbothioamide, 69%, 76°–9°, ethanol Calculated for $C_{20}H_{22}ClN_3S_2$: C, 59.46; H, 5.49; N, 10.40. Found: C, 59.67; H, 5.58; N, 10.37.

EXAMPLE 43

2-(4-Butylphenylimino)-N-(3-chlorophenyl)-5-methyl-3-thiazolidinecarbothioamide, 65%, 83°–4°, ethanol Calculated for $C_{21}H_{24}ClN_3S_2$: C, 60.34; H, 5.79; N, 10.05. Found: C, 60.54; H, 5.83; N, 9.86.

EXAMPLE 44

N-(3-Chlorophenyl)-2-(4-methoxyphenylimino)-3-thiazolidinecarbothioamide, 13%, 133°–5°, aqueous ethanol The reaction was carried out in the presence of 2 ml. of triethylamine.

Calculated for $C_{17}H_{16}ClN_3OS_2$: C, 54.03; H, 4.27; N, 11.12. Found: C, 53.82; H, 4.35; N, 11.28.

EXAMPLE 45

N-(3-Chlorophenyl)-2-(4-methoxyphenylimino)-5-methyl-3-thiazolidinecarbothioamide, 33%, 73°–5°, ethanol Calculated for $C_{18}H_{18}ClN_3OS_2$: C, 55.16; H, 4.63; N, 10.72. Found (average of two runs): C, 55.64; H, 4.72; N, 10.47.

EXAMPLE 46

N-(3-Chlorophenyl)-2-(4-ethoxyphenylimino)-3-thiazolidinecarbothioamide, 28%, 98°–100°, ethanol The reaction was carried out in the presence of 2 ml. of triethylamine.

Calculated for $C_{18}H_{18}ClN_3OS_2$: C, 55.16; H, 4.63; N, 10.72. Found: C, 54.98; H, 4.44; N, 10.51.

EXAMPLE 47

N-(3-Chlorophenyl)-2-(4-butoxyphenylimino)-3-thiazolidinecarbothioamide, 34%, 96°–7°, ethanol The reaction was carried out in the presence of 2 ml. of triethylamine.

Calculated for $C_{20}H_{22}ClN_3OS_2$: C, 57.20; H, 5.28; N, 10.00. Found: C, 57.08; H, 5.18; N, 9.91.

EXAMPLE 48

N-(3-Chlorophenyl)-5-methyl-2-(2-methylthiophenylimino)-3-thiazolidinecarbothioamide, 49%, 119°–21°, ethanol Calculated for $C_{18}H_{18}ClN_3S_3$: C, 52.99; H, 4.45; N, 10.30. Found: C, 52.92; H, 3.97; N, 10.52.

EXAMPLE 49

2-(4-Butylthiophenylimino)-N-(3-fluorophenyl)-3-thiazolidinecarbothioamide, 12% 75°–7°, hexane The reaction was carried out in the presence of a catalytic amount of triethylenediamine. Purification involved chromatographing the material on a silica gel column with benzene as eluant.

Calculated for $C_{20}H_{22}FN_3S_3$: C, 57.25; H, 5.28; N, 10.01. Found: C, 56.95; H, 5.36; N, 9.88.

EXAMPLE 50

N-(3-Chlorophenyl)-5-methyl-2-(2-trifluoromethylphenylimino)-3-thiazolidinecarbothioamide, 49%, 98°–100°, aqueous ethanol Calculated for $C_{18}H_{15}ClF_3N_3S_2$: C, 50.29; H, 3.52; N, 9.77. Found: C, 50.44; H, 3.57; N, 9.79.

EXAMPLE 51

N-(3-Chlorophenyl)-2-(3-trifluoromethylphenylimino)-3-thiazolidinecarbothioamide, 55%, 120°–1°, benzene/hexane Calculated for $C_{17}H_{13}ClF_3N_3S_2$: C, 49.10; H, 3.15; N, 10.10. Found: C, 48.81; H, 3.32; N, 9.85.

EXAMPLE 52

N-(3-Chlorophenyl)-5-methyl-2-(3-trifluoromethylphenylimino)-3-thiazolidinecarbothioamide, 40%, 96°–8°, hexane Calculated for $C_{18}H_{15}ClF_3N_3S_2$: C, 50.29; H, 3.52; N, 9.77. Found: C, 50.37; H, 3.62; N, 9.18.

EXAMPLE 53

N-(3-Chlorophenyl)-5-methyl-2-(4-trifluoromethylphenylimino)-3-thiazolidinecarbothioamide, 19%, 92°–5°, ethanol Calculated for $C_{18}H_{15}ClF_3N_3S_2$: C, 50.29; H, 3.52; N, 9.77. Found: C, 50.49; H, 3.52; N, 9.76.

EXAMPLE 54

N-(3-Chlorophenyl)-2-(2-fluorophenylimino)-5-methyl-3-thiazolidinecarbothioamide, 18%, 77°–9°, aqueous ethanol Calculated for $C_{17}H_{15}ClFN_3S_2$: C, 53.75; H, 3.98; N, 11.06. Found: C, 53.60; H, 4.18; N, 10.98.

EXAMPLE 55

N-(3-Chlorophenyl)-2-(2-chlorophenylimino)-3-thiazolidinecarbothioamide, 13%, 117°–8°, aqueous ethanol Calculated for $C_{16}H_{13}Cl_2N_3S_2$: C, 50.26; H, 3.43; N, 10.99. Found: C, 50.30; H, 3.53; N, 11.11.

EXAMPLE 56

2-(3-Chlorophenylimino)-N-(3-trifluoromethylphenyl)-3-thiazolidinecarbothioamide, 21%, 108°–9°, benzene/hexane The reaction was carried out in the presence of 1 g. of sodium carbonate.

Calculated for $C_{17}H_{13}ClF_3N_3S_2$: C, 49.10; H, 3.15; N, 10.10. Found (average of two runs): C, 49.41; H, 3.45; N, 10.25.

EXAMPLE 57

N-(3-Chlorophenyl)-2-(4-chlorophenylimino)-3-thiazolidinecarbothioamide, 37%, 92°–4°, aqueous ethanol Calculated for $C_{16}H_{13}Cl_2N_3S_2$: C, 50.26; H, 3.43; N, 10.99. Found: C, 50.30; H, 3.73; N, 10.84.

EXAMPLE 58

2-(2-Bromophenylimino)-N-(3-chlorophenyl)-5-methyl-3-thiazolidinecarbothioamide, 50%, 112°–4°, ethanol Calculated for $C_{17}H_{15}BrClN_3S_2$: C, 46.32; H, 3.43; N, 9.53. Found: C, 46.39; H, 3.53; N, 9.67.

EXAMPLE 59

2-(3-Bromophenylimino)-N-(3-chlorophenyl)-5-methyl-3-thiazolidinecarbothioamide, 39%, 112°–3°, ethanol Calculated for $C_{17}H_{15}BrClN_3S_2$: C, 46.32; H, 3.43; N, 9.53. Found: C, 46.09; H, 3.20; N, 9.75.

EXAMPLE 60

2-(4-Bromophenylimino)-N-(3-chlorophenyl)-5-methyl-3-thiazolidinecarbothioamide, 45%, 85°–7°, ethanol Prior to recrystallization, the product was chromatographed on silica gel with benzene as eluant.

Calculated for $C_{17}H_{15}BrClN_3S_2$: C, 46.32; H, 3.43; N, 9.53. Found: C, 46.46; H, 3.45; N, 9.53.

EXAMPLE 61

N-(3-Chlorophenyl)-2-(3-cyanophenylimino)-3-thiazolidinecarbothioamide, 23%, 95°–7°, ethanol Calculated for $C_{17}H_{13}ClN_4S_2$: C, 54.76; H, 3.51; N, 15.02. Found: C, 54.63; H, 3.75; N, 15.13.

EXAMPLE 62

N-(3-Chlorophenyl)-2-(2,3-dimethylphenylimino)-5-methyl-3-thiazolidinecarbothioamide, 67%, 116°–8°, ethanol Calculated for $C_{19}H_{20}ClN_3S_2$: C, 58.52; H, 5.17; N, 10.78. Found: C, 58.31; H, 5.14; N, 10.79.

EXAMPLE 63

N-(3-Chlorophenyl)-2-(2,4-dimethylphenylimino)-5-methyl-3-thiazolidinecarbothioamide, 54%, 97°–9°, ethanol Calculated for $C_{19}H_{20}ClN_3S_2$: C, 58.52; H, 5.17; N, 10.78. Found: C, 58.40; H, 5.38; N, 10.70.

EXAMPLE 64

N-(3-Chlorophenyl)-2-(2,5-dimethylphenylimino)-5-methyl-3-thiazolidinecarbothioamide, 56%, 98°–100°, ethanol Calculated for $C_{19}H_{20}ClN_3S_2$: C, 58.52; H, 5.17; N, 10.78. Found: C, 58.30; H, 5.33; N, 10.66.

EXAMPLE 65

N-(3-Chlorophenyl)-2-(2,6-dimethylphenylimino)-3-thiazolidinecarbothioamide, 18%, 159°–61°, benzene/hexane The reaction was carried out in the presence of a catalytic amount of triethylenediamine.

Calculated for $C_{18}H_{18}ClN_3S_2$: C, 57.51; H, 4.83; N, 11.18. Found: C, 57.50; H, 4.88; N, 11.33.

EXAMPLE 66

N-(3-Chlorophenyl)-2-(2,4-dichlorophenylimino)-3-thiazolidinecarbothioamide, 22%, 118°–9°, aqueous ethanol Calculated for $C_{16}H_{12}Cl_3N_3S_2$: C, 46.11; H, 2.90; N, 10.08. Found: C, 45.87; H, 3.17; N, 10.23.

EXAMPLE 67

2-(2,6-Dichlorophenylimino)-N-(3-fluorophenyl)-3-thiazolidinecarbothioamide, 26%, 124°–6°, benzene/hexane The reaction was carried out in the presence of a catalytic amount of triethylenediamine.

Calculated for $C_{16}H_{12}Cl_2FN_3S_2$: C, 48.01; H, 3.02; N, 10.50. Found: C, 47.83; H, 2.71; N, 10.69.

EXAMPLE 68

N-(3-Chlorophenyl)-5-methyl-2-(2,4,5-trimethylphenylimino)-3-thiazolidinecarbothioamide, 57%, 112°–4°, ethanol

EXAMPLE 69

N-(3-Chlorophenyl)-2-cyclohexylmethylimino-5-methyl-3-thiazolidinecarbothioamide, 26%, 82°–4°, hexane Calculated for $C_{18}H_{24}ClN_3S_2$: C, 56.60; H, 6.33; N, 11.00. Found: C, 56.59; H, 6.55; N, 10.85.

EXAMPLE 70

2-Benzylimino-N-(3-chlorophenyl)-3-thiazolidinecarbothioamide, 78%, 88°–9°, benzene/hexane.

The reaction was carried in the presence of a catalytic amount of triethylenediamine.

Calculated for $C_{17}H_{16}ClN_3S_2$: C, 56.42; H, 4.46; N, 11.61. Found: C, 56.18; H, 4.66; N, 11.31.

EXAMPLE 71

N-(3-Chlorophenyl)-2-phenethylimino-3-thiazolidinecarbothioamide, 4%, 78°–9°, chloroform/hexane.

Calculated for $C_{18}H_{18}ClN_3S_2$: C, 57.51; H, 4.83; N, 11.18. Found: C, 57.27; H, 4.65; N, 11.35.

EXAMPLE 72

N-(3-Chlorophenyl)-5-methyl-2-(3-phenylpropylimino)-3-thiazolidinecarbothioamide, 5%, 71°–3°, ethanol Prior to recrystallization, the product was chromatographed on silica gel with benzene as eluant.

Calculated for $C_{20}H_{22}ClN_3S_2$: C, 59.46; H, 5.49; N, 10.40. Found: C, 59.67; H, 5.62; N, 10.23.

EXAMPLE 73

N-(3-Chlorophenyl)-2-diphenylmethylimino-5-methyl-3-thiazolidinecarbothioamide, 31%, 96°-8°, ethanol Calculated for $C_{24}H_{22}ClN_3S_2$: C, 63.77; H, 4.91; N, 9.30. Found: C, 63.48; H, 5.06; N, 9.08.

EXAMPLE 74

N-(3-Fluorophenyl)-5-methyl-2-(2-pyridylimino)-3-thiazolidinecarbothioamide, 22%, 103°-4°, benzene/hexane The reaction was carried out in the presence of a catalytic amount of triethylenediamine.

Calculated for $C_{16}H_{15}FN_4S_2$: C, 55.47; H, 4.36; N, 16.17. Found: C, 55.29; H, 4.41; N, 15.97.

EXAMPLE 75

N-(3-Chlorophenyl)-5-methyl-2-(2-pyridylimino)-3-thiazolidinecarbothioamide, 41%, 117°-9°, ethanol.

Calculated for $C_{16}H_{15}ClN_4S_2$: C, 52.96; H, 4.17; N, 15.44. Found: C, 52.89; H, 4.15; N, 15.68.

EXAMPLE 76

N-(3-Chlorophenyl)-5-methyl-2-(3-pyridylimino)-3-thiazolidinecarbothioamide, 44%, 101°-4°, ethanol.

Calculated for $C_{16}H_{15}ClN_4S_2$: C, 52.96; H, 4.17; N, 15.44. Found: C, 53.21; H, 4.20; N, 15.16.

EXAMPLE 77

N-(3-Chlorophenyl)-5-methyl-2-(6-methyl-2-pyridylimino)-3-thiazolidinecarbothioamide, 40%, 106°-7°, ethanol.

The reaction was carried out in the presence of 4 ml. of triethylamine.

Calculated for $C_{17}H_{17}ClN_4S_2$: C, 54.17; H, 4.55; N, 14.86. Found: C, 54.47; H, 4.33; N, 14.63.

EXAMPLE 78

N-(3-Chlorophenyl)-2-(6-methoxy-3-pyridylimino)-5-methyl-3-thiazolidinecarbothioamide, 33%, 94°-6°, ethanol Calculated for $C_{17}H_{17}ClN_4OS_2$: C, 51.97; H, 4.36; N, 14.26. Found: C, 51.73; H, 4.13; N, 13.99.

EXAMPLE 79

N-(3-Chlorophenyl)-2-(5-chloro-2-pyridylimino)-5-methyl-3-thiazolidinecarbothioamide, 45%, 101°-3°, chloroform/hexane.

The reaction was carried out in the presence of a catalytic amount of triethylenediamine.

Calculated for $C_{16}H_{14}Cl_2N_4S_2$: C, 48.36; H, 3.55; N, 14.10. Found: C, 48.16; H, 3.27; N, 13.99.

EXAMPLE 80

N-(3-Chlorophenyl)-5-methyl-2-piperidinoimino-3-thiazolidinecarbothioamide, 40%, 91°-3°, ethanol Calculated for $C_{16}H_{21}ClN_4S_2$: C, 52.09; H, 5.74; N, 15.19. Found: C, 51.79; H, 5.50; N, 15.33.

EXAMPLE 81

N-(3-Chlorophenyl)-5-methyl-2-morpholinoimino-3-thiazolidinecarbothioamide, 97%, 117°-9°, benzene/hexane Calculated for $C_{15}H_{19}ClN_4OS_2$: C, 48.57; H, 5.16; N, 15.10. Found: C, 48.73; H, 5.11; N, 15.05.

EXAMPLE 82

N-(3-Chlorophenyl)-5-methyl-2-(2-pyrazinylimino)-3-thiazolidinecarbothioamide, 33%, 106°-8°, ethanol Calculated for $C_{15}H_{14}ClN_5S_2$: C, 49.51; H, 3.88; N, 19.25. Found: C, 49.49; H, 4.05; N, 19.05.

EXAMPLE 83

N-(3-Chlorophenyl)-5-methyl-2-tetrahydrofurfurylimino-3-thiazolidinecarbothioamide, 28%, 64°-5°, benzene/hexane.

Calculated for $C_{16}H_{20}ClN_3OS_2$: C, 51.95; H, 5.45; N, 11.36. Found: C, 52.19; H, 5.25; N, 11.43.

EXAMPLE 84

N-(3-Chlorophenyl)-2-phenylhydrazono-3-thiazolidinecarbothioamide, 22%, 122°-3°, benzene/hexane Calculated for $C_{16}H_{15}ClN_4S_2$: C, 52.96; H, 4.17; N, 15.44. Found: C, 52.86; H, 3.94; N, 15.36.

EXAMPLE 85

N-(3-Chlorophenyl)-2-diphenylhydrazono-3-thiazolidinecarbothioamide, 139°-40°, ethanol Calculated for $C_{22}H_{19}ClN_4S_2$: C, 60.19; H, 4.36; N, 12.76. Found: C, 60.45; H, 4.43; N, 12.52.

EXAMPLE 86

Preparation of N-(3-trifluoromethylphenyl)-2-(3-trifluoromethylphenylimino)-3-thiazolidinecarbothioamide A mixture of 6.1 g. of m-trifluoromethylphenyl isothiocyanate, 6.8 g. of 2-bromoethylamine hydrobromide, 3.5 g. of sodium carbonate, and about 100 ml. of chloroform was stirred at ambient temperature for about 14 hours. To the reaction mixture was added about 50 ml. of water. The aqueous phase was washed with chloroform which was added to the organic phase. The organic phase then was washed with saturated aqueous sodium chloride and dried over anhydrous magnesium sulfate. After filtering, the solvent was removed under reduced pressure. The residue was recrystallized from petroleum ether to give N-(3-trifluoromethylphenyl)-2-(3-trifluoromethylphenylimino)-3-thiazolidinecarbothioamide, m.p. 116°-7°.

Calculated for $C_{18}H_{13}F_6N_3S_2$: C, 48.10; H, 2.92; N, 9.35. Found: C, 48.38; H, 3.07; N, 9.26.

EXAMPLE 87

Preparation of N-(3-fluorophenyl)-2-(3-fluorophenylimino)-3-thiazolidinecarbothioamide The procedure of Example 86 was repeated, except that the reactants consisted of 9.2 g. of 3-fluorophenyl isothiocyanate, 6.2 g. of 2-bromoethylamine hydrobromide, and 3.2 g. of sodium carbonate. The residue remaining after removal of solvent was recrystallized from benzene/hexane, giving 8.4 g. (80%) of N-(3- fluorophenyl)-2-(3-fluorophenylimino)-3-thiazolidinecarbothioamide, m.p. 108°–9°.

Calculated for $C_{16}H_{13}F_2N_3S_2$: C, 55.00; H, 3.75; N, 12.03. Found: C, 54.59; H, 3.89; N, 12.01.

EXAMPLE 88

Preparation of N-(3-chlorophenyl)-2-(3-chlorophenylimino)-3-thiazolidinecarbothioamide The procedure of Example 86 was repeated, except that the reactants consisted of 6.8 g. of m-chlorophenyl isothiocyanate, 4.1 g. of 2-bromoethylamine hydrobromide, and 2.2 g. of sodium carbonate. The residue remaining after removal of the solvent was recrystallized first from benzene/hexane and then from benzene, giving 1.3 g. (17%) of N-(3-chlorophenyl)-2-(3-chlorophenylimino)-3-thiazolidinecarbothioamide, m.p. 121°–3°.

Calculated for $C_{16}H_{13}Cl_2N_3S_2$: C, 50.26; H, 3.43; N, 10.99; S, 16.77; Cl, 18.55. Found: C, 49.98; H, 3.20; N, 10.84; S, 16.27; Cl, 18.56.

As already indicated, the structures of the compounds of the present invention were determined in part by nuclear magnetic resonance ananlyses. In view of the controversy regarding the structures of compounds of this type, however, a sample of the compound of Example 50 was subjected to X-ray analysis.

Small prismatic needles suitable for X-ray work were crystallized from a mixture of ethanol and water. The crystals belonged to the centric space group $P\bar{1}$, with two molecules in the unit cell having the dimensions:

$a = 8.331 \pm 0.002$ Å
$b = 11.230 \pm 0.004$ Å
$c = 11.624 \pm 0.003$ Å
$\alpha = 114.19 \pm 0.03°$
$\beta = 92.46 \pm 0.02°$
$\gamma = 102.09 \pm 0.03°$ Intensities for 2,618 independent reflections ($2\theta_{max} = 115°$) were measured using Cu X-radiation.

The structure was solved by direct phasing techniques using the computer program MULTAN (P. Main et al., MULTAN. A Computer Program for the Automatic Solution of Crystal Structures, University of York, England, 1974) and by subsequent Fourier syntheses. The current level of refinement using full-matrix least-squares is $R = 0.117$.

The structure of the compound of Example 50 was observed to be N-(3-chlorophenyl)-5-methyl-2-(2-trifluoromethylphenylimino)-3-thiazolidinecarbothioamide, thereby confirming the structure already assigned on the basis of elemental microanalysis and nuclear magnetic resonance analysis.

The compounds of the present invention are useful for the control of insect pests. For example, the compounds are active against such insects as Mexican bean beetle, boll weevil, corn rootworm, cereal leaf beetle, flea beetle, borers, Colorado potato beetle, grain beetles, alfalfa weevil, carpet beetle, confused flour beetle, powder post beetle, wireworms, rice weevil, rose beetle, plum curculio, white grubs, melon aphid, rose aphid, white fly, grain aphid, corn leaf aphid, pea aphid, mealy-bugs, scales, leafhopper, citrus aphid, spotted alfalfa aphid, green peach aphid, bean aphid, milkweed bug, tarnished plant bug, box elder bug, bed bug, squash bug, chinch bug, housefly, yellow-fever mosquito, stable fly, horn fly, cabbage maggot, carrot rust fly, codling moth, cutworm, clothes moth, Indian meal moth, leafrollers, corn earworm, European corn borer, cabbage looper, cotton bollworm, bagworm, sod webworm, fall armyworm, German cockroach, and American cockroach.

Because the compounds of the present invention appear to function most effectively when ingested by the target insect, such compounds are particularly useful for the control of insect pests on plants, and especially for the control of Mexican bean beetles. In general, however, the compounds of the present invention can be applied to or incorporated into any food or water source for the target insect.

Thus, the present invention provides a method for reducing or eradicating a population of an insect species which comprises administering to the insect by ingestion an insecticidally-effective amount of a compound of the present invention. The present invention further provides a method for reducing or eradicating a population of the insect species *Epilachna varivestis* which comprises administering to the insect by ingestion an insecticidally-effective amount of a compound of the present invention.

The term "insecticidally-effective amount" refers to an amount which results in the inactivation of the insect. Such inactivation can be lethal, either immediately or with delay, or it can be a sub-lethal inactivation in which the insect is rendered incapable of carrying out one or more of its normal life processes. Thus, the term "reducing or eradicating" means that the compound of the present invention can either kill all of the insect species to which the compound is administered, or that the administration of the compound reduces the population of such insect species. As is well known in the art, many known insecticides render the insect incapable of carrying out one or more of its normal life processes. Most often, the nervous system typically is seriously disturbed. However, the precise mechanism by which the compounds constituting the present invention operate is not yet known, and the insecticidal methods of the present invention are not limited by any mode of operation.

The utilization of an inactivating amount of one of the compounds of the present invention is critical to the insecticidal methods of the present invention. The inactivating amount can sometimes be administered by employing the compound in unmodified form. However, for best results, it generally is necessary that the compound or compounds be employed in modified form; that is, as one component of a composition formulated to implement the insecticidal effects. Thus, for example, the active ingredient can be mixed with water or other liquid or liquids, preferably aided by the usage of a surface-active agent. The compounds also can be incorporated on finely-divided solid, which can be a substance having surface-active adsorption properties, to yield a wettable powder which subsequently can be dispersed in water or other liquid, or incorporated as part of a dust which can be applied directly. Other methods of formulation are known in the art and can be employed in implementing the present invention.

The exact concentration of one or more of the compounds of the present invention in a composition thereof with one or a plurality of adjuvants can vary; it is necessary only that one or more of the products be present in such amount as to make possible the application of an inactivating dosage to an insect. In many situations, a composition comprising about 0.001 percent by weight of the present active agent is effective for the administration of an inactivating amount thereof to insect pests. Compositions having a higher concentration of active agent, such as a concentration of from about 0.001 to about 0.5 percent can, of course, be employed. In still other operations, compositions containing from about 0.5 to about 98 percent by weight of one or more compounds are conveniently employed. Such compositions are adapted to be employed as treating compositions per se or as concentrates for subsequent dilution with additional adjuvant to produce ultimate treating compositions.

Liquid compositions containing the desired amount of active agent are prepared by dissolving the substance in an organic liquid or by dispersing the substance in water with or without the aid of a suitable surface-active dispersing agent such as an ionic or nonionic emulsifying agent. Such compositions also can contain modifying substances which serve to aid spreading and adhesion of the material on plant foliage. Suitable organic liquid carriers include the agricultural spray oils and the petroleum distillates such as diesel fuel, kerosine, fuel oil, naphthas, and Stoddard solvent. Among such liquids the petroleum distillates are generally preferred. The aqueous compositions can contain one or more water-immiscible solvents for the toxicant compound. In such aqueous compositions, the carrier comprises an aqueous emulsion, e.g., a mixture of water, emulsifying agent, and water-immiscible solvent. The choice of dispersing and emulsifying agent and the amount thereof employed is dictated by the nature of the composition and by the ability of the agent to facilitate the dispersing of the active agent in the carrier to produce the desired composition. Dispersing and emulsifying agents which can be employed in the compositions include the condensation products of alkylene oxides with phenols and organic acids, alkaryl sulfonates, polyoxyalkylene derivatives of sorbitan esters, complex ether alcohols, and the like. For a review of known surface-active agents which are suitably employed in implementing the present invention, attention is directed to U.S. Pat. No. 3,095,299, second column, lines 25-36, and references cited therein.

In the preparation of dust compositions, the active ingredient is intimately dispersed in and on a finely-divided solid such as clay, talc, chalk, gypsum, limestone, vermiculite fines, perlite, and the like. In one method of achieving such dispersion, the finely divided carrier is mechanically mixed or ground with the active agent.

Similarly, dust compositions containing the toxicant compounds can be prepared with various of solid carriers such as bentonite, fuller's earth, attapulgite, and other clays having surface-active adsorption properties. Depending upon the proportions of ingredients, these dust compositions can be employed as concentrates and subsequently diluted with additional adsorptive-type solid carriers or with chalk, talc, or gypsum, or the like to obtain the desired amount of active ingredient in a composition adapted to be employed in accordance with the present invention. Also, such dust compositions can be dispersed in water, with or without the aid of a dispersing agent, to form spray mixtures.

The compositions of the present invention also can be employed in granular formulations. These formulations are prepared in conventional manner, typically by dissolving the compound in a solvent with or without a surface-active agent and spraying or otherwise distributing the resulting solution onto pre-formed granules. Such granular formulations are capable of providing longer-lasting activity and may be preferred for crops such as corn where repeated application is not practical.

When operating in accordance with the present invention, one or more of the compounds or a composition containing one or more of the compounds is applied to a source of food or water for the pest to be controlled in any convenient manner, for example, by means of hand dusters or sprayers or by simple mixing with the food to be ingested by the pests. Application to the foliage of plants is conveniently carried out with power dusters, boom sprayers, and fog sprayers. In such foliar applications, the employed composition should not contain any appreciable amounts of any phytotoxic diluents. In large-scale operations, dust or low volume sprays can be applied from the air. The present invention also comprehends the employment of compositions comprising one or more of compounds of the present invention, an adjuvant, and one or more other biologically-active materials, such as other insecticides, fungicides, miticides, bacteriocides, nematocides, and the like.

It is usual in describing foliar applications of plant protectants to measure the application rate by the concentration of dispersion in which it is applied. The application rate is measured in this way because it is customary to apply a sufficient amount of the dispersion to cover the foliage with a thin film. The amount of dispersion applied is thus dependent on the foliar area of the plant, and the quantity of plant-protecting compound is dependent upon its concentration in the dispersion.

Thus, in one embodiment, the insecticidal methods are carried out by applying the compounds to the foliage of plants or other source of food for the insect, and applications are made in the same manner as already described. The insecticidal application rates are from about 10 ppm to about 2000 ppm. It is, of course, apparent that higher or lower concentrations can be employed, depending upon the insect species to be controlled, the plant or other food source to which application is to be made, and the potency or toxicity of the particular compound in the composition.

The activity of representative compounds of the present invention against Mexican bean bettle is illustrated by the following example.

EXAMPLE 89

The compounds to be tested were dissolved or suspended in 50:50 acetone:ethanol, and a blend of anionic and nonionic surfactants was added. The solution then was dispersed in water, so that the final dispersion contained about 20 percent of solvent and the concentration of test compound shown in the table below.

The test compound dispersions were sprayed on the foliage of young bean plants in an amount sufficient to wet the foliage completely. The dispersions then were allowed to dry, and individual leaves were removed from the plants. The petiole of each leaf was wrapped in water-soaked cotton and the leaf then was infested with second instar larva of Mexican bean beetle. Five larva were applied to each leaf, and two replicates were used for each compound concentration. Mortality was observed on the fourth and seventh days after treatment. Untreated control insects were included with every group of test insects.

Insect mortality produced by the compound was rated on a scale where 0 represented no morality, 1 represented less than 50 percent mortality, 2 represented 51-99 percent mortality, and 3 represented 100 percent mortality of insects. Results were averaged where a compound was tested repeatedly against the insect. Empty spaces in the table indicate that the compound was not tested at the indicated rate. The results produced by typical compounds of the invention are summarized in Table 1 which follows.

TABLE 1

ACTIVITY OF REPRESENTATIVE COMPOUNDS AGAINST MEXICAN BEAN BEETLE

| Compound of Example | ORIGINAL TEST | | | | RETEST | | | | |
|---|---|---|---|---|---|---|---|---|---|
| | 1000 ppm. | | 100 ppm. | | 100 ppm. | 50 ppm. | 25 ppm. | 10 ppm. | 5 ppm. |
| | 4 days | 7 days | 4 days | 7 days | 7 days | 7 days | 7 days | 7 days | 7 days |
| 1 | 3 | 3 | 2 | 2 | | | | | |
| 2 | 3 | 3 | 3 | 3 | 2 | 1 | 0 | | |
| 3 | 3 | 3 | 3 | 3 | 2 | 1 | 1 | | |
| 4 | 3 | 3 | 3 | 3 | 3 | 2 | 2 | 1 | |
| 5 | 2 | 3 | 2 | 3 | 2 | 1 | 1 | | |
| 6 | 3 | 3 | 3 | 3 | | | | | |
| 7 | 3 | 3 | 3 | 3 | 2 | 1 | 1 | 2 | |
| 8 | 3 | 3 | | | | | | | |
| 9 | 3 | 3 | 2 | 3 | 3 | 2 | 1 | 1 | |
| 10 | 3 | 3 | 3 | 3 | 3 | 2 | 2 | 0 | |
| 11 | 3 | 3 | 0 | 0 | | | | | |
| 12 | 3 | 3 | 3 | 3 | 3 | 3 | 1 | | 1 |
| 13 | 3 | 3 | 2 | 3 | 3 | 2 | 1 | | |
| 14 | 2 | 3 | 3 | 3 | 2 | 1 | 1 | | |
| 15 | 3 | 3 | 3 | 3 | 2 | 1 | 1 | 1 | 1 |
| 16 | 3 | 3 | 3 | 3 | 3 | 3 | 2 | 1 | 1 |
| 17 | 3 | 3 | 0 | 3 | 2 | 1 | 1 | | |
| 18 | 3 | 3 | 3 | 3 | 3 | | 2 | 2 | 2 |
| 19 | 3 | 3 | 2 | 2 | 3 | 3 | 2 | | |
| 20 | 3 | 3 | 2 | 3 | 3 | 3 | 2 | 1 | |
| 21 | 3 | 3 | 3 | 3 | 2 | 2 | 2 | 1 | |
| 22 | 2 | 2 | 0 | 2 | 2 | 1 | 0 | | |
| 23 | 3 | 3 | 1 | 2 | 3 | 1 | 1 | 1 | |
| 24 | 1 | 2 | 0 | 0 | | | | | |
| 25 | 3 | 3 | 3 | 3 | 3 | 3 | 2 | 1 | 1 |
| 26 | 3 | 3 | 3 | 3 | 3 | 2 | 2 | | |
| 27 | 3 | 3 | 3 | 3 | | | | | |
| 28 | 2 | 3 | 0 | 0 | | | | | |
| 29 | 3 | 3 | 3 | 3 | 3 | 3 | 2 | 1 | 1 |
| 30 | 2 | 3 | | | | | | | |
| 31 | 3 | 3 | 3 | 3 | 3 | 2 | 2 | 0 | |
| 32 | 3 | 3 | 3 | 3 | 3 | 3 | 2 | 2 | 1 |
| 33 | 3 | - | 3 | 3 | 2 | 3 | 1 | 0 | 2 |
| 34 | 3 | 3 | 2 | 3 | 3 | 2 | 1 | 0 | |
| 35 | 2 | 3 | 1 | 3 | 2 | 1 | 1 | 0 | |
| 36 | 3 | 3 | 3 | 3 | 3 | 3 | 3 | 1 | |
| 37 | 3 | 3 | 3 | 3 | 3 | 2 | 1 | 1 | |
| 38 | 3 | 3 | 3 | 3 | 3 | 2 | 2 | 1 | 1 |
| 39 | 3 | 3 | 3 | 3 | 3 | 2 | 1 | | |
| 40 | 3 | 3 | 3 | 3 | 3 | 2 | 2 | 1 | |
| 41 | 3 | 3 | 3 | 3 | 3 | 3 | 2 | 0 | 1 |
| 42 | 3 | 3 | 3 | 3 | 3 | 3 | 3 | 1 | 1 |
| 43 | 3 | 3 | 3 | 3 | 3 | 3 | 3 | 1 | |
| 44 | 3 | 3 | 1 | 3 | 3 | 3 | 2 | 2 | 1 |
| 45 | 3 | 3 | 3 | 3 | | | | | |
| 46 | 3 | 3 | 3 | 3 | 3 | 3 | 3 | 1 | 1 |
| 47 | 3 | 3 | 3 | 3 | 2 | 3 | 2 | 1 | |
| 48 | 1 | 3 | 0 | 1 | | | | | |
| 49 | 3 | 3 | 1 | 2 | | | | | |
| 50 | 3 | 3 | 2 | 2 | | | | | |
| 51 | 1.5 | 2.5 | 0.5 | 3 | 2 | 2 | 2 | 1 | |
| 52 | 3 | 3 | 2 | 3 | 3 | 2 | 0 | | |
| 53 | 3 | 3 | 3 | 3 | 3 | 3 | 2 | 0 | 1 |
| 54 | 3 | 3 | 3 | 3 | 1 | 1 | 1 | 1 | |
| 55 | 3 | 3 | 3 | 3 | 3 | 2 | 2 | | |
| 56 | 3 | 3 | 3 | 3 | 3 | 2 | 1 | 0 | |
| 57 | 3 | 3 | 3 | 3 | 3 | 2 | 2 | | |
| 58 | 3 | 3 | 2 | 3 | 2 | 2 | 1 | 1 | |
| 59 | 3 | 3 | 0 | 0 | | | | | |
| 60 | 0 | 3 | 0 | 1 | | | | | |
| 61 | 3 | 3 | 3 | 3 | | 1 | 0 | 0 | 0 |
| 62 | 3 | 3 | 2 | 3 | 3 | 3 | 2 | 1 | |
| 63 | 3 | 3 | 3 | 3 | 3 | 2 | 2 | 1 | |
| 64 | 3 | 3 | 3 | 3 | 3 | 3 | 1 | 1 | |
| 65 | 3 | 3 | 1 | 1 | | | | | |
| 66 | 3 | 3 | 2 | 3 | 3 | 2 | 2 | | |
| 67 | 0 | 1 | 0 | 0 | | | | | |
| 68 | 3 | 3 | 3 | 3 | 3 | 3 | 3 | 1 | |
| 69 | 3 | 3 | 3 | 3 | 3 | 3 | 2 | 1 | 0 |
| 70 | 3 | 3 | | | | | | | |
| 71 | 3 | 3 | 3 | 3 | 3 | 2 | 1 | | |
| 72 | 3 | 3 | 3 | 3 | 3 | 2 | 1 | 1 | |

TABLE 1-continued

ACTIVITY OF REPRESENTATIVE COMPOUNDS AGAINST MEXICAN BEAN BEETLE

| Compound of Example | ORIGINAL TEST | | | | RETEST | | | | |
|---|---|---|---|---|---|---|---|---|---|
| | 1000 ppm. | | 100 ppm. | | 100 ppm. | 50 ppm. | 25 ppm. | 10 ppm. | 5 ppm. |
| | 4 days | 7 days | 4 days | 7 days | 7 days | 7 days | 7 days | 7 days | 7 days |
| 73 | 3 | 3 | 3 | 3 | 3 | 2 | | 1 | 1 |
| 74 | 3 | 3 | 0 | 1 | | | | | |
| 75 | 3 | 3 | 0 | 2 | | | | | |
| 76 | 3 | 3 | 3 | 3 | | | | | |
| 77 | 3 | 3 | 2 | 3 | 2 | 1 | 1 | | |
| 78 | 3 | 3 | 1 | 2 | 2 | 1 | 1 | | |
| 79 | 3 | 3 | 0 | 0 | | | | | |
| 80 | 3 | 3 | 3 | 3 | 3 | 3 | 1 | | |
| 81 | 3 | 3 | 2 | 2 | | | | | |
| 82 | 3 | 3 | 3 | 3 | 2 | 2 | 1 | 1 | |
| 83 | 3 | 3 | 3 | 3 | 2 | 1 | 1 | 1 | |
| 84 | 3 | 3 | 1 | 2 | 3 | 3 | 2 | | |
| 85 | | 3 | | | | | | | |
| 86 | 2.5 | 2.5 | 2 | 3 | | | | | |
| 87 | 3 | 3 | 2 | 3 | 3 | 2 | 1 | 0 | |
| 88 | 0 | 3 | 0 | 1 | | | | | |

The activities of representative compounds of the present invention against several other species of insects are demonstrated by the following examples.

EXAMPLE 90

Activity against yellow-fever mosquito

Each test compound was formulated by dissolving 10 mg. of the compound in 1 ml. of acetone and mixing the resultant solution with a quantity of water sufficient to give a volume of 100 ml., giving a test solution having a test compound concentration of 100 ppm. The test solutions having lower concentrations of test compound then were obtained by serial dilution of the 100 ppm solution with water. The test solutions were placed in 100 ml. glass beakers or, alternatively, 6 oz. plastic containers, with 40 ml. of test solution per beaker or container and two beakers or containers per concentration. Twenty to thirty 24-hour mosquito larvae, *Aedes aegypti*, were placed in each beaker or container. The larvae were fed 10-20 mg. of pulverized Purina Laboratory Chow daily for seven days. During this time, the beakers or containers were kept in a room in which the temperature and relative humidity were maintained at about 26° and about 51 percent, respectively.

After seven days, the percent mortalities (percent control) of the mosquito larvae were determined by visual observation of the number of living larvae. All treatments were compared to solvent and nontreated controls. The results are set forth in Table 2, which follows:

TABLE 2

ACTIVITY OF REPRESENTATIVE COMPOUNDS AGAINST YELLOW-FEVER MOSQUITO LARVAE

| Compound of Example | Concentration, ppm | Percent Control |
|---|---|---|
| 12 | 10 | 100 |
| 17 | 10 | 90 |
| 21 | 10 | 100 |
| 25 | 10 | 90 |
| 38 | 10 | 100 |
| 41 | 10 | 95 |
| 47 | 10 | 50 |
| 71 | 10 | 100 |

EXAMPLE 91

Activity against black blowfly

Each test compound was formulated by dissolving 4 mg. of the compound in 0.4 ml. of acetone and mixing the resultant solution with 40 g. of homogenized beef liver to give a mixture containing 100 ppm of test compound. Prior to homogenizing in a blender, the liver was prepared by trimming off excess fat and connective tissue.

Mixtures containing lower concentrations of test compounds were prepared in an analogous manner. Thus, 1 mg. of a test compound, dissolved in 0.4 ml. of acetone and mixed with 40 g. of homogenized beef liver, gave a mixture containing 25 ppm of test compound. To prepare a mixture containing 10 ppm, 5 mg. of a test compound was dissolved in 0.5 ml. of acetone. A 0.1-ml. aliquot of this solution was diluted to 1 ml. with acetone, and a 0.4-ml. aliquot of this second solution was mixed with 40 g. of homogenized beef liver.

Eight oz. hot drink cups were filled one-third full with Ab-sorb-dri (small animal bedding). Each batch of treated homogenized liver was divided between two cups and the liver in each cup was infested with 20 two-day-old blowfly larvae, *Phormia regina*. Additional Ab-sorb-dri was added to each cup which then was capped with a perforated lid.

A cup containing liver mixed with the solvent, acetone, and a cup containing liver to which neither test compound nor solvent were added, also were prepared to serve as a solvent control and an untreated control, respectively. The control cups otherwise were handled as described above.

All of the cups were maintained in a room wherein the temperature and relative humidity were controlled at about 26° and about 51 percent, respectively, until the control larvae pupated. All pupae then were removed from the cups and placed in 100×20 mm. plastic petri dishes and held until adult flies emerged.

The number of pupae per cup was recorded at the time the pupae were placed in the petri dishes. The number of emerged adults per dish also was recorded. In each case, the precent control was calculated by means of the following formula:

$$\% \text{ Control} = \frac{\text{No. survivors in untreated control} - \text{No. survivors in treatment}}{\text{No. survivors in untreated control}} \times 100$$

The test results are summarized in Table 3.

TABLE 3
ACTIVITY OF REPRESENTATIVE COMPOUNDS AGAINST BLACK BLOWFLY LARVAE

| Compound of Example | Concentration, ppm | Percent Control |
|---|---|---|
| 12 | 100 | 18 |
| 21 | 25 | 6 |
| 32 | 100 | 5 |
| 38 | 25 | 9 |
| 47 | 100 | 16 |
| 71 | 10 | 1 |

The compounds of Examples 32 and 47 also were tested against black blowfly larvae in a modified test, described below.

One mg. of each test compound was placed in a 15-ml. test tube. To each test tube then were added 1 ml. of N,N-dimethylformamide and 9 ml. of distilled water, giving a stock solution containing 100 ppm of test compound. A 10 ppm test solution of each compound then was prepared by adding to a 6.5-ml. test tube 0.2 ml. of stock solution and 1.8 ml. of bovine serum. A dental wick then was placed in each 6.5-ml. test tube. Approximately 50 blowfly larvae were placed on the center of each dental wick. Each test tube was lightly stoppered with cotton and incubated at 27° for 24 hours.

After the 24-hour incubation period, each wick was removed and the larvae were washed from the test tube and wick with tepid water into a black dish. The number of live larvae in each case were counted. Non-treated larvae in tubes containing only a solvent-serum medium were examined first to adjust for normal mortality. The percent control was calculated and represents the ratio, expressed as a percentage, of dead larvae to the total larval population. The compounds of Examples 32 and 47 showed no activity by this modified test.

EXAMPLE 92

Activity against yellow mealworm

Test compound, 30 mg., was dissolved in 3 ml. of acetone and the resulting solution was mixed thoroughly with 30 g. of insect wheat germ diet (Vanderzant Adkisson insect wheat germ diet, Nutrition Biochemicals). The diet mixture, containing 1000 ppm of test compound, then was spread on waxed paper and allowed to stand in an open room for one hour to allow the acetone to evaporate. A diet mixture containing 100 ppm of test compound was prepared in a similar manner, using 3 mg. of test compound. A control diet mixture also was prepared by mixing 3 ml. of acetone with 30 g. of insect wheat germ diet and handling the resultant mixture as already described.

Each diet mixture, including the control mixture, was divided among four 100×20 mm. plastic petri dishes. Two of the dishes were infested with ten yellow mealworm larvae, *Tenebrio molitor*, 0.25 inch long, per dish. The other two dishes were similarly infested, except that the larvae were 0.75-1 inch long. The dishes were kept in a room in which the temperature and relative humidity were maintained at about 26° and about 51 percent, respectively.

After seven days, the dishes infested with 0.25-inch larvae were observed. The percent control in each case was calculated as described in Example 91. The results obtained are summarized in Table 4.

TABLE 4
ACTIVITY OF REPRESENTATIVE COMPOUNDS AGAINST YELLOW MEALWORM LARVAE

| Compound of Example | Concentration, ppm | Percent Control |
|---|---|---|
| 2 | 1000 | 100 |
| 12 | 1000 | 100 |
|  | 500 | 90 |
| 38 | 1000 | 60 |
| 71 | 1000 | 90 |
|  | 500 | 85 |
| 73 | 1000 | 100 |

EXAMPLE 93

Activity against confused flour beetle

The formulation of each test compound and the control was carried out essentially as described in Example 92. To prepare a diet mixture containing 100 ppm of test compound, 3 mg. of test compound was dissolved in 3 ml. of acetone and 2 ml. of the resulting solution was mixed with insect wheat germ diet. The remaining 1 ml. of solution was diluted to 10 ml. with additional acetone and a 2-ml. aliquot of this second solution was mixed with 20 g. of diet to give a mixture containing 10 ppm of test compound.

Each batch of diet was divided among three 60×15 mm. plastic petri dishes. Each dish was infested with 20-30 confused flour beetle adults. As in Example 92, all dishes were maintained at 26° and 51 percent relative humidity.

After seven days, the dishes were observed and percent control calculated as described in Example 91. Table 5 summarizes the results of the test.

TABLE 5
ACTIVITY OF REPRESENTATIVE COMPOUNDS AGAINST CONFUSED FLOUR BEETLE

| Compound of Example | Concentration, ppm | Percent Control |
|---|---|---|
| 12 | 100 | 6 |
| 21 | 100 | 10 |
| 38 | 10 | 10 |
| 71 | 100 | 6 |

EXAMPLE 94

Activity against housefly

Each test compound, 3 mg., was dissolved in 1 ml. of acetone and diluted to a volume of 30 ml. with stock sugar solution, giving a test sugar solution containing 100 ppm of test compound. Test solutions containing lower concentrations were prepared by appropriate dilutions of aliquots of the 100 ppm solution. The stock sugar solution was prepared by dissolving 200 g. of sugar in 500 ml. of water.

To a one-inch square of cell-o-cotton in a 100×10 mm. plastic petri dish was added by pipette 3 ml. of test solution, with three replicates being prepared per concentration. Three control replicates containing no test compound also were prepared. To each dish was added 20-30 housefly adults. The covered dishes were maintained at 26° and 51 percent relative humidity for 24 hours, after which time the dishes were observed. Percent control was calculated as the ratio, expressed as a percentage, of dead or moribund flies to initial fly population after adjusting for normal mortality as determined by the control replicates. The results of the test are presented in Table 6.

TABLE 6
ACTIVITY OF REPRESENTATIVE COMPOUNDS AGAINST HOUSEFLY ADULTS

| Compound of Example | Concentration, ppm | Percent Control |
|---|---|---|
| 12 | 100 | 93 |
|  | 50 | 20 |
| 18 | 100 | 11 |
| 38 | 100 | 20 |
| 71 | 100 | 20 |

From the foregoing, it is apparent that various of the compounds of the present invention are effective against yellow-fever mosquito larvae, yellow mealworm larvae, housefly adults, and, to a lesser extent, blowfly larvae and confused flour beetle adults. The compounds of the present invention clearly are especially effective against the Mexican bean beetle. The compounds of the present invention do not appear to be active against the Southern armyworm, however.

What is claimed is:

1. A compound of the formula,

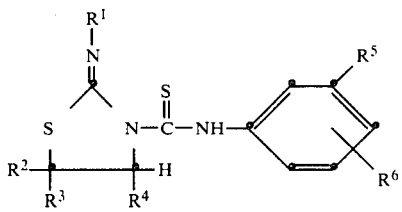

wherein
$R^1$ represents
(A) $C_1$–$C_{18}$ alkyl;
(B) $C_2$–$C_{18}$ alkenyl;
(C) $C_4$–$C_{18}$ alkadienyl;
(D) $C_3$–$C_{12}$ cycloalkyl, optionally substituted with either one or two $C_1$–$C_4$ alkyl groups;
(E) $C_5$–$C_{12}$ cycloalkenyl, optionally substituted with either one or two $C_1$–$C_3$ alkyl groups;
(F) $C_6$–$C_{12}$ cycloalkadienyl, optionally substituted with either one or two $C_1$–$C_3$ alkyl groups;
(G) phenyl, optionally substituted with from one to three groups selected from the group consisting of
  (1) $C_1$–$C_6$ alkyl,
  (2) $C_1$–$C_6$ alkoxy,
  (3) $C_1$–$C_6$ alkylthio,
  (4) trifluoromethyl,
  (5) halo, and
  (6) cyano;
(H) (cycloalkyl)alkyl, containing no more than about 18 carbon atoms, in which the cycloalkyl moiety is as defined herein above;
(I) phenylalkyl, containing no more than about 18 carbon atoms, in which the phenyl moiety is as defined hereinabove;
(J) diphenylalkyl, containing no more than about 18 carbon atoms, in which each phenyl moiety is as defined hereinabove;
(K) pyridyl, optionally substituted with either one or two groups selected from the group consisting of
  (1) $C_1$–$C_3$ alkyl,
  (2) $C_1$–$C_3$ alkoxy, or
  (3) halo;
(L) piperidino, optionally substituted with either one or two $C_1$–$C_3$ alkyl groups;
(M) morpholino;
(N) pyrazinyl, optionally substituted with either one or two $C_1$–$C_3$ alkyl groups;
(O) pyridylalkyl, containing no more than about 17 carbon atoms, in which the pyridyl moiety is as defined hereinabove;
(P) piperidinoalkyl, containing no more than about 17 carbon atoms, in which the piperidino moiety is as defined hereinabove;
(Q) morpholinoalkyl, containing no more than about 16 carbon atoms;
(R) pyrazinylalkyl, containing no more than about 16 carbon atoms, in which the pyrazinyl moiety is as defined hereinabove;
(S) tetrahydrofurylalkyl, containing no more than about 17 carbon atoms; and
(T) substituted amino, having the formula

in which $R^8$ and $R^9$ independently are selected from the group consisting of hydrogen, $C_1$–$C_{18}$ alkyl, phenyl, and phenylalkyl, wherein the phenyl and phenylalkyl moieties are as defined hereinabove, provided that at least one of $R^8$ and $R^9$ is other than hydrogen;

$R^2$ and $R^3$ independently are selected from the group consisting of
(A) hydrogen,
(B) $C_1$–$C_3$ alkyl, and
(C) phenyl, with the proviso that when one of $R^2$ and $R^3$ is phenyl, the other of $R^2$ and $R^3$ is hydrogen;

$R^4$ represents
(A) hydrogen or
(B) $C_1$–$C_3$ alkyl;

$R^5$ represents
(A) halo,
(B) trifluoromethyl,
(C) cyano, or
(D) 1,1,2,2-tetrafluoroethoxy; and $R^6$ represents
(A) hydrogen,
(B) halo, or
(C) $C_1$–$C_3$ alkyl;

with the provisos that when $R^5$ is bromo, $R^1$ can not be 3-bromophenyl; when $R^5$ is cyano, $R^1$ can not be 3-cyanophenyl; when $R^5$ is halo and $R^6$ is halo, $R^6$ can not be in the 2-position; and when $R^5$ is halo and $R^6$ is $C_1$–$C_3$ alkyl, $R^6$ can not be in the 4-position.

2. A compound of claim 1, wherein $R^1$ is selected from the group consisting of 3-pyridyl; phenylamino and diphenylalkyl, in which each phenyl moiety is unsubstituted; cycloalkyl; and phenyl, optionally monosubstituted with chloro, trifluoromethyl, $C_1$–$C_3$ alkyl, or $C_1$–$C_4$ alkoxy.

3. A compound of claim 1, wherein $R^1$ is either $C_6$–$C_8$ cycloalkyl, or phenyl optionally monosubstituted with $C_1$–$C_3$ alkyl or $C_1$–$C_4$ alkoxy in the 2- or 4-position, or trifluoromethyl in the 3- or 4-position.

4. A compound of claim 1, wherein one of $R^2$ and $R^3$ is $C_1$–$C_3$ alkyl and the other of $R^2$ and $R^3$ is hydrogen.

5. A compound of claim 1, wherein one of $R^2$ and $R^3$ is methyl and the other of $R^2$ and $R^3$ is hydrogen.

6. A compound of claim 1, wherein $R^4$ is hydrogen, methyl, or ethyl.

7. A compound of claim 1, wherein $R^4$ is hydrogen.

8. A compound of claim 1, wherein $R^5$ is chloro, bromo, or trifluoromethyl.

9. A compound of claim 1, wherein $R^5$ is chloro.

10. The compound of claim 1, which compound is N-(3-chlorophenyl)-2-cyclohexylimino-3-thiazolidinecarbothioamide.

11. The compound of claim 1, which compound is N-(3-chlorophenyl)-2-diphenylmethylimino-5-methyl-3-thiazolidinecarbothioamide.

12. The compound of claim 1, which compound is N-(3-chlorophenyl)-2-phenylimino-3-thiazolidinecarbothioamide.

13. The compound of claim 1, which compound is N-(3-chlorophenyl)-4-ethyl-2-phenylimino-3-thiazolidinecarbothioamide.

14. The compound of claim 1, which compound is N-(3-chlorophenyl)-5-methyl-2-phenylimino-3-thiazolidinecarbothioamide.

15. The compound of claim 1, which compound is N-(3-chlorophenyl)-2-(o-tolylimino)-3-thiazolidinecarbothioamide.

16. The compound of claim 1, which compound is N-(3-chlorophenyl)-5-methyl-2-(o-tolylimino)-3-thiazolidinecarbothioamide.

17. The compound of claim 1, which compound is N-(3-chlorophenyl)-2-(2-ethylphenylimino)-3-thiazolidinecarbothioamide.

18. The compound of claim 1, which compound is N-(3-chlorophenyl)-2-(4-ethylphenylimino)-5-methyl-3-thiazolidinecarbothioamide.

19. The compound of claim 1, which compound is N-(3-trifluoromethylphenyl)-2-(3-trifluoromethylphenylimino)-3-thiazolidinecarbothioamide.

20. The compound of claim 1, which compound is N-(3-chlorophenyl)-5-methyl-2-(4-trifluoromethylphenylimino)-3-thiazolidinecarbothioamide.

21. The compound of claim 1, which compound is N-(3-chlorophenyl)-2-(4-methoxyphenylimino)-3-thiazolidinecarbothioamide.

22. The compound of claim 1, which compound is N-(3-chlorophenyl)-2-(4-methoxyphenylimino)-5-methyl-3-thiazolidinecarbothioamide.

23. The compound of claim 1, which compound is N-(3-chlorophenyl)-2-(4-ethoxyphenylimino)-3-thiazolidinecarbothioamide.

24. The compound of claim 1, which compound is N-(3-chlorophenyl)-5-methyl-2-(3-pyridylimino)-3-thiazolidinecarbothioamide.

25. The compound of claim 1, which compound is N-(3-chlorophenyl)-2-(4-butoxyphenylimino)-3-thiazolidinecarbothioamide.

26. The compound of claim 1, which compound is N-(3-chlorophenyl)-2-(4-ethylphenylimino)-5-methyl-3-thiazolidinecarbothioamide.

27. The compound of claim 1, which compound is N-(3-chlorophenyl)-2-(3-ethylphenylimino)-5-methyl-3-thiazolidinecarbothioamide.

28. The compound of claim 1, which compound is 2-phenylimino-N-(3-trifluoromethylphenyl)-3-thiazolidinecarbothioamide.

29. The compound of claim 1, which compound is N-(3-chlorophenyl)-2-(2-chlorophenylimino)-3-thiazolidinecarbothioamide.

30. The compound of claim 1, which compound is N-(3-chlorophenyl)-5-methyl-2-piperidinoimino-3-thiazolidinecarbothioamide.

31. The compound of claim 1, which compound is N-(3-bromophenyl)-2-phenylimino-3-thiazolidinecarbothioamide.

32. A method for reducing or eradicating a population of an insect species which comprises administering to the insect by ingestion an insecticidally-effective amount of a compound of claim 1.

33. A method of claim 32, wherein $R^1$ is selected from the group consisting of 3-pyridyl; phenylamino and diphenylamino, in which each phenyl moiety is unsubstituted; cycloalkyl; and phenyl, optionally monosubstituted with chloro, trifluoromethyl, $C_1$–$C_3$ alkyl, or $C_1$–$C_4$ alkoxy.

34. A method of claim 32, wherein $R^1$ is either $C_6$–$C_8$ cycloalkyl, or phenyl optionally monosubstituted with $C_1$–$C_3$ alkyl or $C_1$–$C_4$ alkoxy in the 2- or 4-position, or trifluoromethyl in the 3- or 4-position.

35. A method of claim 32, wherein one of $R^2$ and $R^3$ is methyl and the other of $R^2$ and $R^3$ is hydrogen, $R^4$ is hydrogen, and $R^5$ is chloro, bromo, or trifluoromethyl.

36. A method for reducing or eradicating a population of the insect species *Epilachna varivestis* which comprises administering to the insect by ingestion an insecticidally-effective amount of a compound of claim 1.

37. A method of claim 36, wherein $R^1$ is selected from the group consisting of 3-pyridyl; phenylamino and diphenylalkyl, in which each phenyl moiety is unsubstituted; cycloalkyl; and phenyl, optionally monosubstituted with chloro, trifluoromethyl, $C_1$–$C_3$ alkyl, or $C_1$–$C_4$ alkoxy.

38. A method of claim 36, wherein $R^1$ is either $C_6$–$C_8$ cycloalkyl, or phenyl optionally monosubstituted with $C_1$–$C_3$ alkyl or $C_1$–$C_4$ alkoxy in the 2- or 4-position, or trifluoromethyl in the 3 or 4-position.

39. A method of claim 36, wherein one of $R^2$ and $R^3$ is $C_1$–$C_3$ alkyl and the other of $R^2$ and $R^3$ is hydrogen.

40. A method of claim 36, wherein one of $R^2$ and $R^3$ is methyl and the other of $R^2$ and $R^3$ is hydrogen.

41. A method of claim 36, wherein $R^4$ is hydrogen, methyl, or ethyl.

42. A method of claim 36, wherein $R^4$ is hydrogen.

43. A method of claim 36, wherein $R^5$ is chloro, bromo, or trifluoromethyl.

44. A method of claim 36, wherein $R^5$ is chloro.

45. The method of claim 36, in which the compound is N-(3-chlorophenyl)-2-cyclohexylimino-3-thiazolidinecarbothioamide.

46. The method of claim 36, in which the compound is N-(3-chlorophenyl)-2-diphenylmethylimino-5-methyl-3-thiazolidinecarbothioamide.

47. The method of claim 36, in which the compound is N-(3-chlorophenyl)-2-phenylimino-3-thiazolidinecarbothioamide.

48. The method of claim 36, in which the compound is N-(3-chlorophenyl)-4-ethyl-2-phenylimino-3-thiazolidinecarbothioamide.

49. The method of claim 36, in which the compound is N-(3-chlorophenyl)-5-methyl-2-phenylimino-3-thiazolidinecarbothioamide.

50. The method of claim 36, in which the compound is N-(3-chlorophenyl)-2-(o-tolylimino)-3-thiazolidinecarbothioamide.

51. The method of claim 36, in which the compound is N-(3-chlorophenyl)-5-methyl-2-(o-tolylimino)-3-thiazolidinecarbothioamide.

52. The method of claim 36, in which the compound is N-(3-chlorophenyl)-2-(2-ethylphenylimino)-3-thiazolidinecarbothioamide.

53. The method of claim 36, in which the compound is N-(3-chlorophenyl)-2-(4-ethylphenylimino)-5-methyl-3-thiazolidinecarbothioamide.

54. The method of claim 36, in which the compound is N-(3-trifluoromethylphenyl)-2-(3-trifluoromethylphenylimino)-3-thiazolidinecarbothioamide.

55. The method of claim 36, in which the compound is N-(3-chlorophenyl)-5-methyl-2-(4-trifluoromethylphenylimino)-3-thiazolidinecarbothioamide.

56. The method of claim 36, in which the compound is N-(3-chlorophenyl)-2-(4-methoxyphenylimino)-3-thiazolidinecarbothioamide.

57. The method of claim 36, in which the compound is N-(3-chlorophenyl)-2-(4-methoxyphenylimino)-5-methyl-3-thiazolidinecarbothioamide.

58. The method of claim 36, in which the compound is N-(3-chlorophenyl)-2-(4-ethoxyphenylimino)-3-thiazolidinecarbothioamide.

59. The method of claim 36, in which the compound is N-(3-chlorophenyl)-5-methyl-2-(3-pyridylimino)-3-thiazolidinecarbothioamide.

60. The method of claim 36, in which the compound is N-(3-chlorophenyl)-2-(4-butoxyphenylimino)-3-thiazolidinecarbothioamide.

61. The method of claim 36, in which the compound is N-(3-chlorophenyl)-2-(4-ethylphenylimino)-5-methyl-3-thiazolidinecarbothioamide.

62. The method of claim 36, in which the compound is N-(3-chlorophenyl)-2-(3-ethylphenylimino)-5-methyl-3-thiazolidinecarbothioamide.

63. The method of claim 36, in which the compound is 2-phenylimino-N-(3-trifluoromethylphenyl)-3-thiazolidinecarbothioamide.

64. The method of claim 36, in which the compound is N-(3-chlorophenyl)-2-(2-chlorophenylimino)-3-thiazolidinecarbothioamide.

65. The method of claim 36, in which the compound is N-(3-chlorophenyl)-5-methyl-2-piperidinoimino-3-thiazolidinecarbothioamide.

66. The method of claim 36, in which the compound is N-(3-bromophenyl)-2-phenylimino-3-thiazolidinecarbothioamide.

67. An insecticidal composition which comprises an insecticidally-effective amount of a compound of claim 1 and an agriculturally-acceptable carrier.

68. A composition of claim 67, wherein $R^1$ is selected from the group consisting of 3-pyridyl; phenylamino and diphenylalkyl, in which each phenyl moiety is unsubstituted; cycloalkyl; and phenyl, optionally monosubstituted with chloro, trifluoromethyl, $C_1$-$C_3$ alkyl, or $C_1$-$C_4$ alkoxy.

69. A composition of claim 67, wherein $R^1$ is either $C_6$-$C_8$ cycloalkyl, or phenyl optionally monosubstituted with $C_1$-$C_3$ alkyl or $C_1$-$C_4$ alkoxy in the 2- or 4-position, or trifluoromethyl in the 3- or 4-position.

70. A composition of claim 67, wherein one of $R^2$ and $R^3$ is $C_1$-$C_3$ alkyl and the other of $R^2$ and $R^3$ is hydrogen.

71. A composition of claim 67, wherein one of $R^2$ and $R^3$ is methyl and the other of $R^2$ and $R^3$ is hydrogen.

72. A composition of claim 67, wherein $R^4$ is hydrogen, methyl, or ethyl.

73. A composition of claim 67, wherein $R^4$ is hydrogen.

74. A composition of claim 67, wherein $R^5$ is chloro, bromo, or trifluoromethyl.

75. A composition of claim 67, wherein $R^5$ is chloro.

76. The composition of claim 67, in which the compound is N-(3-chlorophenyl)-2-cyclohexylimino-3-thiazolidinecarbothioamide.

77. The composition of claim 67, in which the compound is N-(3-chlorophenyl)-2-diphenylmethylimino-5-methyl-3-thiazolidinecarbothioamide.

78. The composition of claim 67, in which the compound is N-(3-chlorophenyl)-2-phenylimino-3-thiazolidinecarbothioamide.

79. The composition of claim 67, in which the compound is N-(3-chlorophenyl)-4-ethyl-2-phenylimino-3-thiazolidinecarbothioamide.

80. The composition of claim 67, in which the compound is N-(3-chlorophenyl)-5-methyl-2-phenylimino-3-thiazolidinecarbothioamide.

81. The composition of claim 67, in which the compound is N-(3-chlorophenyl)-2-(o-tolylimino)-3-thiazolidinecarbothioamide.

82. The composition of claim 67, in which the compound is N-(3-chlorophenyl)-5-methyl-2-(o-tolylimino)-3-thiazolidinecarbothioamide.

83. The composition of claim 67, in which the compound is N-(3-chlorophenyl)-2-(3-ethylphenylimino)-3-thiazolidinecarbothioamide.

84. The composition of claim 67, in which the compound is N-(3-chlorophenyl)-2-(4-ethylphenylimino)-5-methyl-3-thiazolidinecarbothioamide.

85. The composition of claim 67, in which the compound is N-(3-trifluoromethylphenyl)-2-(3-trifluoromethylphenylimino)-3-thiazolidinecarbothioamide.

86. The composition of claim 67, in which the compound is N-(3-chlorophenyl)-5-methyl-2-(4-trifluoromethylphenylimino)-3-thiazolidinecarbothioamide.

87. The composition of claim 67, in which the compound is N-(3-chlorophenyl)-2-(4-methoxyphenylimino)-3-thiazolidinecarbothioamide.

88. The composition of claim 67, in which the compound is N-(3-chlorophenyl)-2-(4-methoxyphenylimino)-5-methyl-3-thiazolidinecarbothioamide.

89. The composition of claim 67, in which the compound is N-(3-chlorophenyl)-2-(4-ethoxyphenylimino)-3-thiazolidinecarbothioamide.

90. The composition of claim 67, in which the compound is N-(3-chlorophenyl)-5-methyl-2-(3-pyridylimino)-3-thiazolidinecarbothioamide.

91. The composition of claim 67, in which the compound is N-(3-chlorophenyl)-2-(4-butoxyphenylimino)-3-thiazolidinecarbothioamide.

92. The composition of claim 67, in which the compound is N-(3-chlorophenyl)-2-(4-ethylphenylimino)-5-methyl-3-thiazolidinecarbothioamide.

93. The composition of claim 67, in which the compound is N-(3-chlorophenyl)-2-(3-ethylphenylimino)-5-methyl-3-thiazolidinecarbothioamide.

94. The composition of claim 67, in which the compound is 2-phenylimino-N-(3-trifluoromethylphenyl)-3-thiazolidinecarbothioamide.

95. The composition of claim 67, in which the compound is N-(3-chlorophenyl)-2-(2-chlorophenylimino)-3-thiazolidinecarbothioamide.

96. The composition of claim 67, in which the compound is N-(3-chlorophenyl)-5-methyl-2-(piperidinoimino)-3-thiazolidinecarbothioamide.

97. The composition of claim 67, in which the compound is N-(3-bromophenyl)-2-phenylimino-3-thiazolidinecarbothioamide.

* * * * *

UNITED STATES PATENT AND TRADEMARK OFFICE
CERTIFICATE OF CORRECTION

PATENT NO. : 4,289,778
DATED : September 15, 1981
INVENTOR(S) : Balko

It is certified that error appears in the above-identified patent and that said Letters Patent are hereby corrected as shown below:

In Table 1, under Retest heading, column 100 ppm., example 30, insert --1--.

In Table 1, under Retest heading, column 100 ppm., example 70, insert --1--.

In Table 1, under Retest heading, column 25 ppm., example 73, insert --2--.

Column 15, example 10, line 43, "methyl3-" should read -- methyl-3- --.

Column 16, example 15, line 17, "methyl3-" should read -- methyl-3- --.

Signed and Sealed this

First Day of June 1982

[SEAL]

Attest:

Attesting Officer

GERALD J. MOSSINGHOFF

Commissioner of Patents and Trademarks